US 8,791,120 B2

(12) United States Patent
MacDonald et al.

(10) Patent No.: US 8,791,120 B2
(45) Date of Patent: Jul. 29, 2014

(54) FAST-DISSOCIATING DOPAMINE 2 RECEPTOR ANTAGONISTS

(75) Inventors: Gregor James MacDonald, Zoersel (BE); Xavier Jean Michel Langlois, Uccle (BE); José Manuel Bartolomé-Nebreda, Toledo (ES); Michiel Luc Maria Van Gool, Madrid (ES)

(73) Assignee: Janssen Pharmaceutica NV, Beerse (BE)

( * ) Notice: Subject to any disclaimer, the term of this patent is extended or adjusted under 35 U.S.C. 154(b) by 0 days.

(21) Appl. No.: 12/526,945

(22) PCT Filed: Feb. 11, 2008

(86) PCT No.: PCT/EP2008/051597
§ 371 (c)(1),
(2), (4) Date: Aug. 12, 2009

(87) PCT Pub. No.: WO2008/098892
PCT Pub. Date: Aug. 21, 2008

(65) Prior Publication Data
US 2010/0069394 A1  Mar. 18, 2010

(30) Foreign Application Priority Data
Feb. 13, 2007  (EP) .................................... 07102222

(51) Int. Cl.
*C07D 403/04* (2006.01)
*A61K 31/50* (2006.01)
*A61P 25/18* (2006.01)

(52) U.S. Cl.
USPC ..................... 514/252.02; 544/238

(58) Field of Classification Search
USPC ..................... 544/238; 514/252.02
See application file for complete search history.

(56) References Cited

U.S. PATENT DOCUMENTS

| 3,933,823 | A | 1/1976 | Denzel et al. |
| 3,933,832 | A | 1/1976 | Langbein et al. |
| 4,126,689 | A | 11/1978 | Sanczuk et al. |
| 4,197,304 | A | 4/1980 | Sanczuk et al. |
| 4,585,471 | A | 4/1986 | Forster et al. |
| 5,461,053 | A | 10/1995 | Boigegrain et al. |
| 5,560,931 | A | 10/1996 | Eickhoff et al. |
| 5,736,545 | A | 4/1998 | Gadwood et al. |
| 5,866,589 | A | 2/1999 | Romero et al. |
| 5,958,923 | A | 9/1999 | Hellendahl et al. |
| 7,335,658 | B2 | 2/2008 | Chakka et al. |
| 7,754,774 | B2 | 7/2010 | Kobayashi et al. |
| 8,058,243 | B2 | 11/2011 | Tyers et al. |
| 2007/0081953 | A1 | 4/2007 | Dahms |
| 2008/0227791 | A1 | 9/2008 | De Bruyn et al. |
| 2010/0063058 | A1 | 3/2010 | MacDonald et al. |
| 2010/0076187 | A1 | 3/2010 | MacDonald et al. |
| 2010/0092505 | A1 | 4/2010 | Bianchi et al. |
| 2010/0120860 | A1 | 5/2010 | MacDonald et al. |
| 2010/0137368 | A1 | 6/2010 | MacDonald et al. |
| 2010/0210687 | A1* | 8/2010 | Cooper et al. ................. 514/321 |
| 2011/0112107 | A1 | 5/2011 | Bartolome-Nebreda et al. |
| 2011/0130408 | A1 | 6/2011 | Bartolme-Nebreda et al. |

FOREIGN PATENT DOCUMENTS

| CA | 2009501 | 8/1990 |
| DE | 2642856 C2 | 3/1977 |
| DE | 3218482 A1 | 11/1983 |
| EP | 0211457 | 2/1987 |
| EP | 0281309 | 9/1988 |
| EP | 0532178 B1 | 3/1993 |
| EP | 1506185 B1 | 2/2005 |
| EP | 1621538 | 2/2006 |
| EP | 1443046 B1 | 12/2008 |
| GB | 1539473 | 1/1979 |
| WO | 95/18118 | 7/1995 |
| WO | 96/02249 | 2/1996 |
| WO | 96/18628 | 6/1996 |
| WO | 9635666 A1 | 11/1996 |
| WO | 97/43279 | 11/1997 |
| WO | WO 99/09025 | 2/1999 |
| WO | 9936407 A1 | 7/1999 |
| WO | 0198273 A1 | 12/2001 |

(Continued)

OTHER PUBLICATIONS

Griesser, in Chapter 8, The Importance of Solvates (pp. 211-230), in the text, Polymorphism: In the Pharmaceutical Industry, Hilfiker, 2006.*
Dean et al., J. Org. Chem. 1993, 58, 7916-7917.
Gillaspy et al., Tetrahedron Letters 1995, 36, 7399-7402.
Goodman et al., Tetrahedron 1999, 55, 15067-15070.
Joyce et al., (2005) Dopamine D3 receptor antagonist as therapeutic agents. Drug Discovery Today 10: 917-925.
Kapur et al., Am. J. Psychiatry 2001, 158:3 p. 360-369.
Leysen et al., Journal of Receptor Research, 1984, 4(7), 817-845.
Mitchell et al., (2005) 5-HT6 receptors: a novel target for cognitive enhancement. Pharmacology & Therapeutics 108:320-333.
Rodefer et al., Neuropsychopharmacology (2007), 1-10).
Tao et al., Tetrahedron Lett. 2003, 44, 7993-7996.

(Continued)

*Primary Examiner* — James O Wilson
*Assistant Examiner* — Cecilia M Jaisle
(74) *Attorney, Agent, or Firm* — Hal B. Woodrow

(57) ABSTRACT

The present invention relates to 4-aryl-6-piperazin-1-yl-3-substituted-pyridazines of formula (I) that are fast dissociating dopamine 2 receptor antagonists, processes for preparing these compounds, pharmaceutical compositions comprising these compounds as an active ingredient. The compounds find utility as medicines for treating or preventing central nervous system disorders, for example schizophrenia, by exerting an antipsychotic effect without motor side effects.

(I)

$$R^6-N\underset{R^4}{\overset{R^5}{\bigcap}}N-\underset{(\phantom{i})_n}{\overset{}{\bigcap}}\underset{R^3}{\overset{N=N}{\bigcap}}\overset{R^1}{\underset{R^2}{}}$$

4 Claims, No Drawings

(56) References Cited

FOREIGN PATENT DOCUMENTS

| WO | 02068409 A1 | 9/2002 |
| WO | 03/045353 | 6/2003 |
| WO | 03049736 A1 | 6/2003 |
| WO | 03062215 A1 | 7/2003 |
| WO | WO 03066604 * | 8/2003 |
| WO | 03072548 A1 | 9/2003 |
| WO | 2004/058729 | 7/2004 |
| WO | 2004/085406 | 10/2004 |
| WO | 2004/098555 | 11/2004 |
| WO | 2005005779 A2 | 1/2005 |
| WO | 2005/011655 | 2/2005 |
| WO | 2005009976 A1 | 2/2005 |
| WO | WO 2005/013907 | 2/2005 |
| WO | 2005/046581 | 5/2005 |
| WO | 2005/077914 | 8/2005 |
| WO | 2005/090317 | 9/2005 |
| WO | 2005105779 A1 | 11/2005 |
| WO | 2005/123692 | 12/2005 |
| WO | 2005/123693 | 12/2005 |
| WO | WO 2005117883 * | 12/2005 |
| WO | 2006034440 A2 | 3/2006 |
| WO | 2006055187 A1 | 5/2006 |
| WO | 2007001975 A1 | 1/2007 |
| WO | 2007048779 A1 | 5/2007 |
| WO | WO 2007130383 * | 11/2007 |
| WO | 2008019967 A2 | 2/2008 |
| WO | 2008/068507 | 6/2008 |
| WO | 2008098892 A1 | 8/2008 |
| WO | 2010012758 A1 | 2/2010 |

OTHER PUBLICATIONS

International Search Report for PCT/EP2008/051597 dated Jun. 19, 2008.
Written Opinion for PCT/EP2008/051597 dated Jun. 19, 2008.
Garzya et al., Bioorganic & Medicinal Chemistry Letters, 17 (2007) 400-405.
Goodman and Gilman's The Pharmacologic Basis of Therapeutics, 12$^{th}$ Edition, Chapter 16, "Pharmacotherapy of Psychosis and Mania" by Jonathan M. Meyer, pp. 417-455, 2011.
Kula et al., CA127:171455 (1997).
Liu et al., Drug Development Research, 70: 145-168 (2009).
International Search Report and Written Opinion, PCT/EP/2008/051597, mailing date Jun. 19, 2008.
PCT counterpart to U.S. Appl. No. 12/091,219, International Search Report, PCT/EP2006/067696, mailing date Jun. 19, 2008.
PCT counterpart to U.S. Appl. No. 12/516,645, International Search Report and Written Opinion, PCT/EP2007/06338, mailing date Dec. 2, 2008.
PCT counterpart to U.S. Appl. No. 12/597,164, International Search Report and Written Opinion, PCT/EP2008/054732, mailing date Sep. 5, 2008.
PCT counterpart to U.S. Appl. No. 12/597,107, International Search Report and Written Opinion, PCT/EP2008/054730, mailing date Jul. 9, 2008.
PCT counterpart to U.S. Appl. No. 12/597,166, International Search Report and Written Opinion, PCT/EP2008/054731, mailing date Sep. 30, 2008.
PCT counterpart to U.S. Appl. No. 13/002,413, International Search Report and Written Opinion, PCT/EP2009/004745, mailing date Aug. 29, 2009.
PCT counterpart to U.S. Appl. No. 13/056,287, International Search Report and Written Opinion, PCT/EP2009/059788, mailing date Sep. 10, 2009.
Abbott, The Molecular Wake-Up Call, Nature, May 24, 2007, pp. 368-370, vol. 447.
Arlt et al, SAR of Novel Biarylmethylamine Dopamine D4 Receptor Ligands, Bioorganic & Medicinal Chemistry Letters, 1998, pp. 2033-2038, vol. 8.
Bartoszyk, Anxiolytic effects of dopamine receptor ligands: I. involvement of dopamine autoreceptors, Life Sciences, 1998, pp. 649-663, vol. 62, No. 7.
Benjamin et al, Pharmacological characterization of recombinant N-type calcium channel (Cav2.2) mediated calcium mobilization using FLIPR, Biochemical Pharmacology, 2006, pp. 770-782, vol. 72.
Bianchi, Recent Withdrawals from CNS Drug Development Trials by Major Pharmaceutical Companies Have Raised Alarm Bells in Scientific and Mental Health Circles, Current Issues in Central Nervous System Drug Development, 2011, pp. 1-6, Suite 101.com.
Binggeli, Phenyl, Pyridine and Quinoline Derivatives as SST5 Receptor Modulators and Their Preparation, Pharmaceutical Compositions and Use in the Treatment of Diseases, CAPLUS, 2008, pp. 1-7, 2008:222500.
Chabner, et al., Antineoplastic Agents, Chemotherapy of Neoplastic Diseases, Neoplastic Agents in, Goodman & Gilman's: The Pharmacological Basis of Therapeutics, 2006, pp. 1315-1403, 11th ed.
Contreras, et al., Aminopyridazines as Acetylcholinesterase Inhibitors, Journal Medicinal Chemistry, 1999, pp. 730-741, vol. 42.
Cook, et al., Preparation of 2-aminophyridine Derivatives as Nitric Oxide Synthase Inhibitors, CAPLUS, 2000, pp. 1-3, 2000:335406.
Dario Braga et al, Making crystals from crystals: a green route to crystal engineering and polymorphism, Chemical Communications, Jun. 15, 2005, pp. 3635-3645, No. 29.
Eichenberger, et al., Heilmittelchemisch Studien in der Heterocyclischen Reihe, Fasciculus, 1956, pp. 1755-1764, vol. 39, No. 208.
Fryatt, et al., Novel Quinolinequinon Antitumor Agents: Structure-Metabolism Studies with NAD(P)H:quinon Oxidoreductase (NQO1), Bioorganic & Medicinal Chemistry, 2004, pp. 1667-1687, vol. 12.
Genin et al, Synthesis and Bioactivity of Novel Bis(heteroaryl)piperazine (BHAP) Reverse Transcriptase Inhibitors: Structure-Activity Relationships and Increased Metabolic Stability of Novel Substituted Pyridine Analogs, Journal of Medicinal Chemistry, 1996, pp. 5267-5275, vol. 39.
Genin et al, Synthesis ans Structure-Activity Relationships of the (Alkylamino)piperidine-Containing BHAP Class of Non-Nucleoside Reverse Transcriptase Inhibitors: Effect of 3-Alkylpyridine Ring Substitution, Journal of Medicinal Chemistry, 1999, pp. 4140-4149, vol. 42.
Grundt, et al., Analogues of the Dopamine D2 Receptor Antagonist L741,626: Binding, Function and SAR, Bioorg Med Chem Lett, Feb. 1, 2007, pp. 745-749, vol. 17, No. 3.
Holenz et al, Medicinal chemistry strategies to 5-HT6receptor ligands as potential cognitive enhancers and antiobesity agents, Drug Discovery Today, Apr. 2006, pp. 283-299, vol. 11, No. 7-8.
Kapitulnik, Drug Transport and Metabolism in the Blood-Brain Barrier, Frontiers in Pharmacology, Jul. 15, 2011, pp. 1-2, vol. 2, Article 37.
Kikuchi, et al., Tetrahydrobenzindoles: Selective Antagonists of the 5-HT7 Receptor, Journal of Medicinal Chemistry, Feb. 25, 1999, pp. 533-535, vol. 42, No. 4.
Kortagere et al, Certain 1,4-Disubstituted Aromatic Piperidines and Piperazines with Extreme Selectivity for the Dopamine D4 Receptor Interact with a Common Receptor Microdomain, Molecular Pharmacology, 2004, pp. 1491-1499, vol. 66, No. 6.
Kula et al, Neuropharmacological assessment of potential dopamine D4 receptor-selective radioligands, European Journal of Pharmacology, 1999, pp. 139-142, vol. 367.
Kula et al, RBI-257: A highly potent dopamine D4 receptor-selective ligand, European Journal of Pharmacology, 1997, pp. 333-336, vol. 331.
Lovenberg et al, Cloning of Rat Histamine H3 Receptor Reveals Distinct Species Pharmacological Profiles, The Journal of Pharmacology and Experimental Therapeutics, 2000, pp. 771-778, vol. 293, No. 3.
Moragues et al, Dopaminergic Activity in a series of N-substituted 2-Aminopyrimidines, II Farmaco, 1980, pp. 951-964, vol. 35, No. 11.
Munson et al, Synthesis of 2-Alkylamino-3-fluoropyridines Using Buchwald Conditions, Synthetic Communications, 2004, pp. 759-766, vol. 34, No. 5.
Okuyama, et al., A Selective Dopamine D4 Receptor Antagonist, NRA0160: A Preclinical Neuropharmacological Profile, Life Sciences, 1999, pp. 2109-2125, vol. 65.

(56) References Cited

OTHER PUBLICATIONS

Phedias, et al., Compositions and Methods for Treating Neurological Disorders or Damage, CAPLUS, 2008, p. 1, 2008:493012.

Poupaert, Drug Design: Basic Principles and Applications, Drug Design: Basic Principles and Applications, 2007, pp. 1362-1370, DOI:10.1081.

Rodefer, Reversal of Subchronic PPC-Induced Deficits in Attentional Set Shifting in Rats by Sertindole and a 5-HT6 Receptor Antagonist: Comparison Among Antipsychotics, Neuropsychopharmacology, 2008, pp. 2657-2666, vol. 33.

Schlachter et al, Substituted 4-aminopiperidines having high in vitro affinity and selectivity for the cloned human dopamine D4 receptor, European Journal of Pharmacology, 1997, pp. 283-286, vol. 322.

Seddon, Pseudopolymorph: A Polemic, 2004, p. 1087, vol. 4, No. 6.

Ten Brink, Preparation of Heterocyclic Compounds for the Treatement of CNS and Cardiovascular Disorders, CAPLUS, 1995, pp. 1-2, 1995:951193.

Vippagunta et al, Crystalline solids, Advanced Drug Delivery Reviews, May 16, 2001, pp. 3-26, vol. 48 No. 1.

WIKIPEDIA, Cell Surface Receptor, Wikipedia, Feb. 2, 2012, pp. 1-6, Wikipedia.

Wood, et al., Aripiprazole Acts as a Selective Dopamine D2 Receptor Partial Agonist, Expert Opin. Investig. Drugs, 2007, pp. 771-775, vol. 16, No. 6.

Xiao et al, Discovery of a series of potent arylthiadiazole H3 antagonists, Bioorganic & Medicinal Chemistry Letters, 2011, pp. 861-864, vol. 21.

Yamada, et al., Involvement of Septal and Striatal Dopamine D-2 Receptors in Yawning Behavior in Rats, Phychopharmacology, 1986, pp. 9-13, vol. 90.

Zablotskaya et al, Silyl Modification of Biologically Active Compounds. 8*. Trimethylsilyl Ethers of Hydroxyl-Containing Thiazole Derivatives, Chemistry of Heterocyclic Compounds, 2002, pp. 859-866, vol. 38, No. 7.

Zhang, et al., Recent Advances Towards the Discovery of Dopamine Receptor Ligands, Expert Opin. Ther. Patents, 2006, pp. 587-630, vol. 16, No. 5.

Fisas et al., British Journal of Pharmacology. 2006, 148: 973-983.

Hannon et al., Acta Biologica Szegediensis. 2002, 46(1-2): 1-12.

* cited by examiner

FAST-DISSOCIATING DOPAMINE 2 RECEPTOR ANTAGONISTS

FIELD OF THE INVENTION

The present invention relates to 4-aryl-6-piperazin-1-yl-3-substituted-pyridazines that are fast dissociating dopamine 2 receptor antagonists, processes for preparing these compounds, pharmaceutical compositions comprising these compounds as an active ingredient. The compounds find utility as medicines for treating or preventing central nervous system disorders, for example schizophrenia, by exerting an antipsychotic effect without motor side effects.

DESCRIPTION OF THE INVENTION

Schizophrenia is a severe and chronic mental illness that affects approximately 1% of the population. Clinical symptoms are apparent relatively early in life, generally emerging during adolescence or early adulthood. The symptoms of schizophrenia are usually divided into those described as positive, including hallucinations, delusions and disorganised thoughts and those referred to as negative, which include social withdrawal, diminished affect, poverty of speech and the inability to experience pleasure. In addition, schizophrenic patients are suffering from cognitive deficits, such as impaired attention and memory. The aetiology of the disease is still unknown, but aberrant neurotransmitter actions have been hypothesized to underlie the symptoms of schizophrenia. The dopaminergic hypothesis is one most often considered; it proposes that hyperactivity of dopamine transmission is responsible for the positive symptoms observed in schizophrenic patients. This hypothesis is based on the observation that dopamine enhancing drugs, such as amphetamine or cocaine, may induce psychosis, and on the correlation that exists between clinical doses of antipsychotics and their potency in blocking dopamine D2 receptors. All marketed antipsychotics mediate their therapeutic efficacy against positive symptoms by blocking the dopamine D2 receptor. Apart from the clinical efficacy, it appears that the major side effects of antipsychotics, such as extrapyramidal symptoms (EPS) and tardive dyskinesia, are also related to dopamine antagonism. Those debilitating side effects appear most frequently with the typical or first generation of antipsychotic (e.g., haloperidol). They are less pronounced with the atypical or second generation of antipsychotic (e.g., risperidone, olanzapine) and even virtually absent with clozapine, which is considered the prototypical atypical antipsychotic. Among the different theories proposed for explaining the lower incidence of EPS observed with atypical antipsychotics, the one that has caught a lot of attention during the last fifteen years, is the multireceptor hypothesis. It follows from receptor binding studies showing that many atypical antipsychotics interact with various other neurotransmitter receptors in addition to dopamine D2 receptors, in particular with the serotonin 5-HT2 receptors, whereas typical antipsychotic like haloperidol bind more selectively to the D2 receptors. This theory has been challenged in recent years because all major atypical antipsychotics fully occupy the serotonin 5-HT2 receptors at clinically relevant dosages but still differ in inducing motor side-effects. As an alternative to the multireceptor hypothesis, Kapur and Seeman ("Does fast dissociation from the dopamine D2 receptor explain the action of atypical antipsychotics?: A new hypothesis", Am. J. Psychiatry 2001, 158:3 p. 360-369) have proposed that atypical antipsychotics can be distinguished from typical antipsychotics by the rates at which they dissociate from dopamine D2 receptors. The fast dissociation from the D2 receptor would make an antipsychotic more accommodating of physiological dopamine transmission, permitting an antipsychotic effect without motor side effects. This hypothesis is particularly convincing when one considers clozapine and quetiapine. These two drugs have the fastest rate of dissociation from dopamine D2 receptors and they carry the lowest risk of inducing EPS in humans. Conversely, typical antipsychotics associated with a high prevalence of EPS, are the slowest dissociating dopamine D2 receptor antagonists. Therefore, identifying new drugs based on their rate of dissociation from the D2 receptor appears a valid strategy to provide new atypical antipsychotics.

As stated previously, current atypical antipsychotics interact with many different neurotransmitter receptors. Some of these interactions (such as the blockade of serotonin 5-HT6 and dopamine D3 receptors) may be beneficial when cognitive impairment and negative symptoms are considered. Indeed, numerous preclinical data have shown that 5-HT6 receptor antagonism has positive effects on cognitive processes in rodents (Mitchell and Neumaier (2005) 5-HT6 receptors: a novel target for cognitive enhancement. Pharmacology & Therapeutics 108:320-333). 5-HT6 antagonism has also been linked to appetite and food intake suppression. Further, D3 receptor antagonism enhances social interaction in rats suggesting a possible benefit on negative symptoms in schizophrenic patients (Joyce and Millan (2005) Dopamine D3 receptor antagonist as therapeutic agents. Drug Discovery Today 10: 917-925). On the other hand, other interactions (such as with adrenergic $\alpha 1$, histamine H1 and serotonin 5-HT2C receptors) are implicated in mediating side-effects, including hypotension, sedation, metabolic disorders and weight gain. Therefore, an additional goal is to combine fast dissociating D2 receptor properties with inhibition of serotonin 5-HT6 and dopamine D3 receptors in the absence of interactions with adrenergic $\alpha 1$, histamine H1 and serotonin 5-HT2C receptors. Such a profile is expected to provide novel compounds efficacious against positive symptoms, negative symptoms and cognitive deficits while having less or none of the major side-effects associated with current antipsychotics.

It is the object of the present invention to provide novel compounds that are fast dissociating dopamine 2 receptor antagonists as well as serotonin 5-HT6 and dopamine D3 receptor antagonists which have an advantageous pharmacological profile as explained hereinbefore, in particular reduced motor side effects, and moderate or negligible interactions with other receptors resulting in reduced risk of developing metabolic disorders.

This goal is achieved by the present novel compounds according to Formula (I):

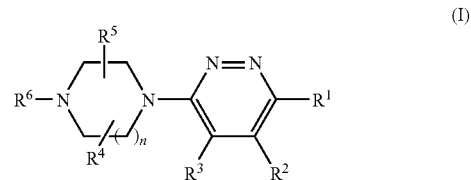

and stereoisomeric forms thereof, wherein $R^1$ is chloro, trifluoromethyl or cyano;

$R^2$ is phenyl; phenyl substituted with 1, 2 or 3 substituents each independently selected from the group consisting of halo, cyano, $C_{1-4}$alkyl, $C_{1-4}$alkyloxy, $C_{1-4}$alkylsulfonyl, perfluoro$C_{1-4}$alkyl, perfluoro$C_{1-4}$alkyloxy, di$C_{1-4}$alkylamino, hydroxyl, and phenyl optionally substituted with 1, 2 or 3 substituents each independently selected from the group consisting of halo, $C_{1-4}$alkyl and perfluoro$C_{1-4}$alkyl; thienyl; thienyl substituted with 1 or 2 substituents each independently selected from the group consisting of halo and $C_{1-4}$alkyl; naphthyl; pyridinyl; pyrrolyl; benzothiazolyl; indolyl; quinolinyl; $C_{3-8}$ cycloalkyl; or $C_{5-7}$cycloalkenyl;

$R^3$ is hydrogen, $C_{1-4}$alkyl, $C_{1-4}$alkyloxy or halo;

$R^4$ and $R^5$ are each independently hydrogen or $C_{1-4}$alkyl, or $R^4$ and $R^5$ together form $C_{1-4}$alkanediyl;

n is 1 or 2; and $R^6$ is hydrogen, $C_{1-4}$alkyl, hydroxy$C_{2-4}$ alkyl, $C_{3-6}$cycloalkyl, $C_{3-6}$cycloalkyl-$C_{1-4}$ alkyl, pyridinylmethyl, or phenylmethyl optionally substituted on the phenyl with 1, 2 or 3 substituents each independently selected from the group consisting of halo, cyano, $C_{1-4}$alkyl, $C_{1-4}$alkyloxy, $C_{1-4}$alkylsulfonyl, perfluoro$C_{1-4}$alkyl, perfluoro$C_{1-4}$alkyloxy and di$C_{1-4}$alkylamino; or $R^5$ and $R^6$ together form $C_{2-5}$alkanediyl;

and the pharmaceutically acceptable salts and solvates thereof.

The compounds according to the invention are fast dissociating D2 receptor antagonists. In addition, the present compounds have approximately the same affinity for dopamine D3 and serotonin 5-HT6 receptors as to dopamine D2 receptors. Insofar as tested, the compounds are antagonists at the three receptor subtypes. This property renders the compounds according to the invention especially suitable for use as a medicine in the treatment or prevention of schizophrenia, schizophreniform disorder, schizoaffective disorder, delusional disorder, brief psychotic disorder, shared psychotic disorder, psychotic disorder due to a general medical condition, substance-induced psychotic disorder, psychotic disorder not otherwise specified; psychosis associated with dementia; major depressive disorder, dysthymic disorder, premenstrual dysphoric disorder, depressive disorder not otherwise specified, Bipolar I disorder, bipolar II disorder, cyclothymic disorder, bipolar disorder not otherwise specified, mood disorder due to a general medical condition, substance-induced mood disorder, mood disorder not otherwise specified; generalized anxiety disorder, obsessive-compulsive disorder, panic disorder, acute stress disorder, post-traumatic stress disorder; mental retardation; pervasive developmental disorders; attention deficit disorders, attention-deficit/hyperactivity disorder, disruptive behaviour disorders; personality disorder of the paranoid type, personality disorder of the schizoid type, personality disorder of the schizotypical type; tic disorders, Tourette's syndrome; substance dependence; substance abuse; substance withdrawal; trichotillomania; and conditions wherein cognition is impaired; Alzheimer's disease, Parkinson's disease, Huntingdon's disease, Lewy Body Dementia, dementia due to HIV disease, dementia due to Creutzfeldt-Jakob disease; amnestic disorders; mild cognitive impairment; and age-related cognitive decline; and feeding disorders such as anorexia and bulimia; and obesity.

A skilled person can make a selection of compounds based on the experimental data provided in the Experimental Part hereinafter. Any selection of compounds is embraced within this invention.

The invention relates to compounds of Formula (I) and stereoisomeric forms thereof, wherein $R^1$ is chloro, trifluoromethyl or cyano;

$R^2$ is phenyl; phenyl substituted with 1, 2 or 3 substituents each independently selected from the group consisting of halo, cyano, $C_{1-4}$alkyl, $C_{1-4}$alkyloxy, $C_{1-4}$alkylsulfonyl, perfluoro$C_{1-4}$alkyl, perfluoro$C_{1-4}$alkyloxy, di$C_{1-4}$alkylamino, hydroxyl, and phenyl substituted with 1, 2 or 3 substituents each independently selected from the group consisting of halo, $C_{1-4}$alkyl and perfluoro$C_{1-4}$alkyl; thienyl; thienyl substituted with 1 or 2 substituents each independently selected from the group consisting of halo and $C_{1-4}$alkyl; naphthyl; pyridinyl; pyrrolyl; benzothiazolyl; indolyl; quinolinyl; $C_{3-8}$ cycloalkyl; or $C_{5-7}$cycloalkenyl;

$R^3$ is hydrogen, $C_{1-4}$alkyl or halo;

$R^4$ and $R^5$ are each independently hydrogen or $C_{1-4}$alkyl, or $R^4$ and $R^5$ together form $C_{1-4}$alkanediyl;

n is 1 or 2; and $R^6$ is hydrogen, $C_{1-4}$alkyl, hydroxy$C_{2-4}$alkyl, $C_{3-6}$cycloalkyl, $C_{3-6}$cycloalkyl$C_{1-4}$alkyl, or phenylmethyl substituted on the phenyl with 1, 2 or 3 substituents each independently selected from the group consisting of halo, cyano, $C_{1-4}$alkyl, $C_{1-4}$alkyloxy, $C_{1-4}$alkylsulfonyl, perfluoro$C_{1-4}$alkyl, perfluoro$C_{1-4}$alkyloxy and di$C_{1-4}$alkylamino; or $R^5$ and $R^6$ together form $C_{2-5}$alkanediyl;

and the pharmaceutically acceptable salts and solvates thereof.

For example, the invention relates to compounds of Formula (I) and stereoisomeric forms thereof, wherein $R^1$ is trifluoromethyl or cyano;

$R^2$ is phenyl; phenyl substituted with 1, 2 or 3 substituents each independently selected from the group consisting of halo, cyano, $C_{1-4}$alkyl, $C_{1-4}$alkyloxy, $C_{1-4}$alkylsulfonyl, perfluoro$C_{1-4}$alkyl, di$C_{1-4}$alkylamino, hydroxyl, and phenyl substituted with 1, 2 or 3 substituents each independently selected from the group consisting of halo, $C_{1-4}$alkyl and perfluoro$C_{1-4}$alkyl; thienyl; thienyl substituted with 1 or 2 substituents each independently selected from the group consisting of halo and $C_{1-4}$alkyl; naphthyl; pyridinyl; pyrrolyl; benzothiazolyl; indolyl; quinolinyl; $C_{3-8}$ cycloalkyl; or $C_{5-7}$cycloalkenyl;

$R^3$ is hydrogen;

$R^4$ and $R^5$ are each independently hydrogen or $C_{1-4}$alkyl;

n is 1;

$R^6$ is hydrogen, methyl, ethyl, cyclopropyl, or phenylmethyl substituted on the phenyl with 1, 2 or 3 substituents each independently selected from the group consisting of halo, cyano, $C_{1-4}$alkyl, $C_{1-4}$alkyloxy, $C_{1-4}$alkylsulfonyl, perfluoro$C_{1-4}$alkyl and di$C_{1-4}$alkylamino; or $R^5$ and $R^6$ together form $C_{2-5}$alkanediyl;

and the pharmaceutically acceptable salts and solvates thereof.

Of particular interest are compounds of Formula (I) and stereoisomeric forms thereof wherein $R^1$ is trifluoromethyl;

$R^2$ is phenyl; phenyl substituted with 1, 2 or 3 substituents each independently selected from the group consisting of halo, cyano, $C_{1-4}$alkyl, $C_{1-4}$alkyloxy, $C_{1-4}$alkylsulfonyl, perfluoro$C_{1-4}$alkyl, di$C_{1-4}$alkylamino, hydroxyl, and phenyl substituted with 1, 2 or 3 substituents each independently selected from the group consisting of halo, $C_{1-4}$alkyl and perfluoro$C_{1-4}$alkyl; thienyl; thienyl substituted with 1 or 2 substituents each independently selected from the group consisting of halo and $C_{1-4}$alkyl; naphthyl; pyridinyl; pyrrolyl; benzothiazolyl; indolyl; quinolinyl; $C_{3-8}$ cycloalkyl; or $C_{5-7}$cycloalkenyl;

$R^3$ is hydrogen;

$R^4$ and $R^5$ are each independently hydrogen or methyl;

n is 1;

$R^6$ is hydrogen, ethyl or (3,5-difluorophenyl)methyl; or $R^5$ and $R^6$ together form 1,3-propanediyl;

and the pharmaceutically acceptable salts and solvates thereof.

Amongst the compounds of Formula (I) and the stereoisomeric forms thereof, the most interesting are, for example, 4-Phenyl-6-piperazin-1-yl-3-trifluoromethyl-pyridazine (E1), 6-(4-Ethylpiperazin-1-yl)-4-phenyl-3-trifluoromethyl-pyridazine (E2), 6-[4-(3,5-Difluorobenzyl)piperazin-1-yl]-4-phenyl-3-trifluoromethyl-pyridazine (E3), 6-(3,5-Dimethylpiperazin-1-yl)-4-phenyl-3-trifluoromethyl-pyridazine (E4), 2-(5-Phenyl-6-trifluoromethyl-pyridazin-3-yl)-octahydro-pyrrolo[1,2-c]pyrazine (E5), 4-(4-Fluorophenyl)-6-piperazin-1-yl-3-trifluoromethyl-pyridazine (E6), 6-piperazin-1-yl-4-thiophen-3-yl-3-trifluoromethyl-pyridazine (E7), 6-piperazin-1-yl-4-o-tolyl-3-trifluoromethyl-pyridazine (E8), 4-(4'-Fluorobiphenyl-4-yl)-6-piperazin-1-yl-3-trifluoromethyl-pyridazine (E9) and 4-Phenyl-6-piperazin-1-yl-pyridazine-3-carbonitrile (E10) and the pharmaceutically acceptable salts and solvates thereof.

Throughout this application, the term "$C_{1-4}$alkyl" when used alone and when used in combinations such as "$C_{1-4}$alkyloxy", "perfluoro$C_{1-4}$alkyl", "di$C_{1-4}$alkylamino", includes, for example, methyl, ethyl, propyl, butyl, 1-methylpropyl, 1,1-dimethylethyl, the term; "perfluoro$C_{1-4}$alkyl" includes for example trifluoromethyl, pentafluoroethyl, heptafluoropropyl and nonafluorobutyl; $C_{3-8}$cycloalkyl includes cyclopropyl, cyclobutyl, cyclopentyl, cyclohexyl, cycloheptyl and cyclooctyl; $C_{5-7}$cycloalkenyl includes cyclopentenyl, cyclohexenyl and cycloheptenyl. The term halo includes fluoro, chloro, bromo, and iodo.

The pharmaceutically acceptable salts are defined to comprise the therapeutically active non-toxic acid addition salts forms that the compounds according to Formula (I) are able to form. Said salts can be obtained by treating the base form of the compounds according to Formula (I) with appropriate acids, for example inorganic acids, for example hydrohalic acid, in particular hydrochloric acid, hydrobromic acid, sulfuric acid, nitric acid and phosphoric acid; organic acids, for example acetic acid, hydroxyacetic acid, propanoic acid, lactic acid, pyruvic acid, oxalic acid, malonic acid, succinic acid, maleic acid, mandelic acid, fumaric acid, malic acid, tartaric acid, citric acid, methanesulfonic acid, ethanesulfonic acid, benzenesulfonic acid, p-toluenesulfonic acid, cyclamic acid, salicylic acid, p-aminosalicylic acid, pamoic acid and mandelic acid. Conversely, said salts forms can be converted into the free forms by treatment with an appropriate base.

The term solvates refers to hydrates and alcoholates which the compounds of Formula (I) may form.

The term "stereochemically isomeric forms" as used hereinbefore defines all the possible isomeric forms that the compounds of Formula (I) may possess. Unless otherwise mentioned or indicated, the chemical designation of compounds denotes the mixture of all possible stereochemically isomeric forms, said mixtures containing all diastereomers and enantiomers of the basic molecular structure. More in particular, stereogenic centers may have the R- or S-configuration; substituents on bivalent cyclic (partially) saturated radicals may have either the cis- or trans-configuration. Compounds encompassing double bonds can have an E or Z-stereochemistry at said double bond. Stereochemically isomeric forms of the compounds of Formula (I) are embraced within the scope of this invention.

The compounds of Formula (I) as prepared in the processes described below may be synthesized in the form of racemic mixtures of enantiomers that can be separated from one another following art-known resolution procedures. The racemic compounds of Formula (I) may be converted into the corresponding diastereomeric salt forms by reaction with a suitable chiral acid. Said diastereomeric salt forms are subsequently separated, for example, by selective or fractional crystallization and the enantiomers are liberated therefrom by alkali. An alternative manner of separating the enantiomeric forms of the compounds of Formula (I) involves liquid chromatography using a chiral stationary phase. Said pure stereochemically isomeric forms may also be derived from the corresponding pure stereochemically isomeric forms of the appropriate starting materials, provided that the reaction occurs stereospecifically. Preferably if a specific stereoisomer is desired, said compound would be synthesized by stereospecific methods of preparation. These methods will advantageously employ enantiomerically pure starting materials.

Pharmacology

In order to find antipsychotic compounds active against positive and negative symptoms and cognitive impairment, and having an improved safety profile (low EPS incidence and no metabolic disorders), we have screened for compounds selectively interacting with the dopamine D2 receptor and dissociating fast from this receptor, and further having affinity for the dopamine D3 receptor as well as the serotonin 5-HT-6 receptor. Compounds were first screened for their D2 affinity in a binding assay using [$^3$H]spiperone and human D2L receptor cell membranes. The compounds showing an $IC_{50}$ less than 10 μM were tested in an indirect assay adapted from a method published by Josee E. Leysen and Walter Gommeren, Journal of Receptor Research, 1984, 4(7), 817-845, to evaluate their rate of dissociation.

The compounds were further screened in a panel of more than 50 common G-protein coupled receptors (CEREP) and found to have a clean profile, that is to have low affinity for the tested receptors, with the exception of the dopamine D3 receptor and the serotonin 5-HT6 receptor.

Some of the compounds have been further tested in in vivo models such as the "Antagonism of apomorphine induced agitation test in rats" and found to be orally active and bioavailable.

Compound E1 was further found to be active in the 'Reversal of subchronic PCP-induced attentional set shifting in rats' test (J. S. Rodefer et al., Neuropsychopharmacology (2007), 1-10).

In view of the aforementioned pharmacology of the compounds of Formula (I), it follows that they are suitable for use as a medicine, in particular for use as an antipsychotic. More especially the compounds are suitable for use as a medicine in the treatment or prevention of schizophrenia, schizophreniform disorder, schizoaffective disorder, delusional disorder, brief psychotic disorder, shared psychotic disorder, psychotic disorder due to a general medical condition, substance-induced psychotic disorder, psychotic disorder not otherwise specified; psychosis associated with dementia; major depressive disorder, dysthymic disorder, premenstrual dysphoric disorder, depressive disorder not otherwise specified, Bipolar I disorder, bipolar II disorder, cyclothymic disorder, bipolar disorder not otherwise specified, mood disorder due to a general medical condition, substance-induced mood disorder, mood disorder not otherwise specified; generalized anxiety disorder, obsessive-compulsive disorder, panic disorder, acute stress disorder, post-traumatic stress disorder; mental retardation; pervasive developmental disorders; attention deficit disorders, attention-deficit/hyperactivity disorder, disruptive behaviour disorders; personality disorder of the paranoid type, personality disorder of the schizoid type, personality disorder of the schizotypical type; tic disorders, Tourette's syndrome; substance dependence; substance abuse; substance withdrawal; trichotillomania. In view of their 5-HT6 antagonistic activity, the compounds of the present invention may further be useful for the treatment or prophylaxis of conditions wherein cognition is impaired; Alzheimer's disease, Parkinson's disease, Huntingdon's disease, Lewy Body Dementia, dementia due to HIV disease, dementia due to Creutzfeldt-Jakob disease; amnestic disorders; mild cognitive impairment; and age-related cognitive decline.

To optimize treatment of patients suffering from a disorder as mentioned in the foregoing paragraph, the compounds of Formula (I) may be administered together with other psychotropic compounds. Thus, in the case of schizophrenia, negative and cognitive symptoms may be targeted.

The present invention also provides a method of treating warm-blooded animals suffering from such disorders, said method comprising the systemic administration of a therapeutic amount of a compound of Formula (I) effective in treating the above described disorders.

The present invention also relates to the use of compounds of Formula (I) as defined hereinabove for the manufacture of a medicament, in particular an antipsychotic medicament, more especially a medicine in the treatment or prevention of schizophrenia, schizophreniform disorder, schizoaffective disorder, delusional disorder, brief psychotic disorder, shared psychotic disorder, psychotic disorder due to a general medical condition, substance-induced psychotic disorder, psychotic disorder not otherwise specified; psychosis associated with dementia; major depressive disorder, dysthymic disorder, premenstrual dysphoric disorder, depressive disorder not otherwise specified, Bipolar I disorder, bipolar II disorder, cyclothymic disorder, bipolar disorder not otherwise specified, mood disorder due to a general medical condition, substance-induced mood disorder, mood disorder not otherwise specified; generalized anxiety disorder, obsessive-compulsive disorder, panic disorder, acute stress disorder, post-traumatic stress disorder; mental retardation; pervasive developmental disorders; attention deficit disorders, attention-deficit/hyperactivity disorder, disruptive behaviour disorders; personality disorder of the paranoid type, personality disorder of the schizoid type, personality disorder of the schizotypical type; tic disorders, Tourette's syndrome; substance dependence; substance abuse; substance withdrawal; trichotillomania; and conditions wherein cognition is impaired; Alzheimer's disease, Parkinson's disease, Huntingdon's disease, Lewy Body Dementia, dementia due to HIV disease, dementia due to Creutzfeldt-Jakob disease; amnestic disorders; mild cognitive impairment; and age-related cognitive decline.

Those of skill in the treatment of such diseases could determine the effective therapeutic daily amount from the test results presented hereinafter. An effective therapeutic daily amount would be from about 0.01 mg/kg to about 10 mg/kg body weight, more preferably from about 0.05 mg/kg to about 1 mg/kg body weight.

The invention also relates to a pharmaceutical composition comprising a pharmaceutically acceptable carrier and, as active ingredient, a therapeutically effective amount of a compound according to Formula (I).

For ease of administration, the subject compounds may be formulated into various pharmaceutical forms for administration purposes. The compounds according to the invention, in particular the compounds according to Formula (I), a pharmaceutically acceptable acid or base addition salt thereof, a stereochemically isomeric form thereof, an N-oxide form thereof and a prodrug thereof, or any subgroup or combination thereof may be formulated into various pharmaceutical forms for administration purposes. As appropriate compositions there may be cited all compositions usually employed for systemically administering drugs. To prepare the pharmaceutical compositions of this invention, an effective amount of the particular compound, optionally in addition salt form, as the active ingredient is combined in intimate admixture with a pharmaceutically acceptable carrier, which carrier may take a wide variety of forms depending on the form of preparation desired for administration. These pharmaceutical compositions are desirable in unitary dosage form suitable, in particular, for administration orally, rectally, percutaneously, by parenteral injection or by inhalation. For example, in preparing the compositions in oral dosage form, any of the usual pharmaceutical media may be employed such as, for example, water, glycols, oils, alcohols and the like in the case of oral liquid preparations such as suspensions, syrups, elixirs, emulsions and solutions; or solid carriers such as starches, sugars, kaolin, diluents, lubricants, binders, disintegrating agents and the like in the case of powders, pills, capsules and tablets. Because of their ease in administration, tablets and capsules represent the most advantageous oral dosage unit forms in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable solutions, for example, may be prepared in which the carrier comprises saline solution, glucose solution or a mixture of saline and glucose solution. Injectable solutions containing compounds of Formula (I) may be formulated in an oil for prolonged action. Appropriate oils for this purpose are, for example, peanut oil, sesame oil, cottonseed oil, corn oil, soybean oil, synthetic glycerol esters of long chain fatty acids and mixtures of these and other oils. Injectable suspensions may also be prepared in which case appropriate liquid carriers, suspending agents and the like may be employed. Also included are solid form preparations that are intended to be converted, shortly before use, to liquid form preparations. In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin. Said additives may facilitate the administration to the skin and/or may be helpful for preparing the desired compositions. These compositions may be administered in various ways, e.g., as a transdermal patch, as a spot-on, as an ointment. Acid or base addition salts of compounds of Formula (I) due to their increased water solubility over the corresponding base or acid form, are more suitable in the preparation of aqueous compositions.

It is especially advantageous to formulate the aforementioned pharmaceutical compositions in unit dosage form for ease of administration and uniformity of dosage. Unit dosage form as used herein refers to physically discrete units suitable as unitary dosages, each unit containing a predetermined quantity of active ingredient calculated to produce the desired therapeutic effect in association with the required pharmaceutical carrier. Examples of such unit dosage forms are tablets (including scored or coated tablets), capsules, pills, powder packets, wafers, suppositories, injectable solutions or suspensions and the like, and segregated multiples thereof.

Since the compounds according to the invention are potent orally administrable compounds, pharmaceutical compositions comprising said compounds for administration orally are especially advantageous.

In order to enhance the solubility and/or the stability of the compounds of Formula (I) in pharmaceutical compositions, it can be advantageous to employ α-, β- or γcyclodextrins or their derivatives, in particular hydroxyalkyl substituted cyclodextrins, e.g. 2-hydroxypropyl-β-cyclodextrin. Also co-solvents such as alcohols may improve the solubility and/or the stability of the compounds according to the invention in pharmaceutical compositions.

Preparation

Compounds of Formula (I) wherein $R^1$ is chloro or trifluoromethyl and $R^2$, $R^3$, $R^4$, $R^5$, $R^6$ and n are as defined before, can be prepared by reacting a compound of Formula (II)

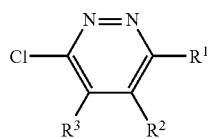

where $R^1$ is chloro or trifluoromethyl and $R^2$ and $R^3$ are as defined before, with a compound of Formula (III)

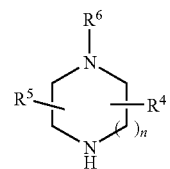

where $R^4$, $R^5$, $R^6$ and n are as defined before, in the presence of a suitable base, such as diisopropylethylamine, in a suitable solvent, such as acetonitrile and under suitable reaction conditions, such as a convenient temperature, either by conventional heating or under microwave irradiation for a period of time to ensure the completion of the reaction.

Compounds of Formula (II) wherein $R^1$ is chloro and $R^2$ and $R^3$ are as defined before, may be prepared by procedures similar to those described in WO-2005/013907.

Compounds of Formula (II) wherein $R^1$ is trifluoromethyl and $R^2$ and $R^3$ are as defined before, can be prepared by reacting a compound of Formula (IV)

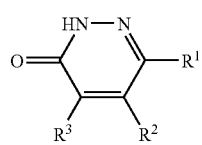

where $R^1$ is trifluoromethyl and $R^2$ and $R^3$ are as defined before, with phosphorous oxychloride, in a suitable solvent, such as acetonitrile, under suitable reaction conditions, such as a convenient temperature, either by conventional heating or under microwave irradiation for a period of time to ensure the completion of the reaction.

Compounds of Formula (IV) wherein $R^1$ is trifluoromethyl and $R^2$ and $R^3$ are as defined before, can be prepared by reacting a compound of Formula (V)

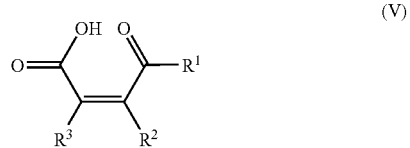

where $R^1$ is trifluoromethyl and $R^2$ and $R^3$ are as defined before, with hydrazine hydrate, in the presence of a suitable catalyst, such as acetic acid, in a suitable solvent, such as acetonitrile, under suitable reaction conditions, such as a convenient temperature, either by conventional heating or under microwave irradiation for a period of time to ensure the completion of the reaction.

Compounds of Formula (V) wherein $R^1$ is trifluoromethyl and $R^2$ and $R^3$ are as defined before, may be prepared by reacting a compound of Formula (VI)

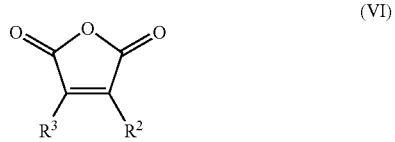

where $R^2$ and $R^3$ are as defined before, with $CF_3SiMe_3$ (VII), in the presence of a suitable catalyst, such as cesium fluoride, in a suitable solvent, such as acetonitrile, under suitable reaction conditions, such as low temperatures, typically ranging between −78° C. and 0° C.

Compounds of Formula (VI) where $R^2$ and $R^3$ are as defined before, can be obtained commercially or by procedures similar to those described in Dean, W. D.; Burn, D. M. J. Org. Chem. 1993, 58, 7916-7917.

Compounds of Formula (I-a)

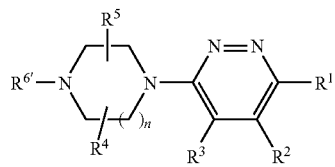

wherein $R^{6'}$ is $R^6$ as defined before but not hydrogen, $R^1$ is chloro or trifluoromethyl and $R^2$, $R^3$, $R^4$, $R^5$ and n are as defined before, can also be prepared by reacting compounds of Formula (I-b)

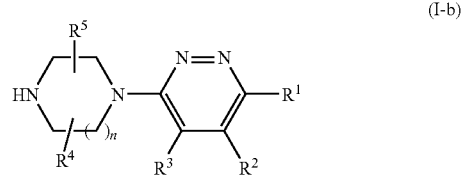

wherein $R^1$ is chloro or trifluoromethyl and $R^2$, $R^3$, $R^4$, $R^5$ and n are as defined before, with a reagent of $R^{6'}$—W wherein $R^{6'}$ is $R^6$ as defined before but not hydrogen and W represents a leaving group such as halo, e.g. chloro, bromo or iodo, or a sulfonyloxy group, e.g. methylsulfonyloxy, trifluoromethylsulfonyloxy, or methylphenylsulfonyloxy in the presence of a base such as diisopropylethylamine, in a suitable solvent such as acetonitrile and under suitable reaction conditions, such as a convenient temperature, either by conventional heating or under microwave irradiation for a period of time to ensure the completion of the reaction.

Alternatively, the compounds of Formula (I-a) wherein $R^{6'}$ is $R^6$ as defined before but not hydrogen, $R^1$ is chloro or trifluoromethyl and $R^2$, $R^3$, $R^4$, $R^5$ and n are as defined before, can also be prepared from a compound of Formula (I-b) wherein $R^1$ is chloro or trifluoromethyl and $R^2$, $R^3$, $R^4$, $R^5$ and n are as defined before, by reductive N-alkylation with an appropriate ketone or aldehyde in the presence of a suitable reducing agent such as sodium triacetoxyborohydride in a suitable solvent such as tetrahydrofuran.

Compounds of Formula (I-b) wherein $R^1$ is chloro or trifluoromethyl and $R^2$, $R^3$, $R^4$, $R^5$ and n are as defined before, may be prepared by deprotection of the protecting group in an intermediate of Formula (VIII)

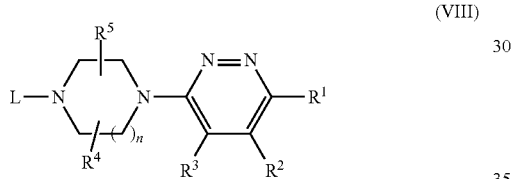

(VIII)

where L represents a suitable protecting group, such as tert-butyloxycarbonyl, $R^1$ is chloro or trifluoromethyl and $R^2$, $R^3$, $R^4$, $R^5$ and n are as defined before, under suitable conditions, such as trifluoroacetic acid in dichloromethane or Amberlyst® 15 ion exchange resin, acidic form in methanol when L represents a tert-butyloxycarbonyl group.

Compounds of Formula (VIII) wherein $R^1$ is chloro or trifluoromethyl and $R^2$, $R^3$, $R^4$, $R^5$ and n are as defined before, can be prepared by reacting a compound of Formula (II) where $R^1$ is chloro or trifluoromethyl and $R^2$ and $R^3$ are as defined before, with a compound of Formula (IX)

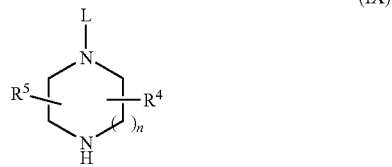

(IX)

where L represents a suitable protecting group, such as tert-butyloxycarbonyl and $R^4$, $R^5$ and n are as defined before, in the presence of a suitable base, such as diisopropylethylamine, in a suitable solvent, such as acetonitrile and under suitable reaction conditions, such as a convenient temperature, either by conventional heating or under microwave irradiation for a period of time to ensure the completion of the reaction.

Compounds of Formula (VIII) wherein $R^1$ is trifluoromethyl and $R^2$, $R^3$, $R^4$, $R^5$ and n are as defined before and L represents a suitable protecting group, such as tert-butyloxycarbonyl, can also be prepared by reacting a compound of Formula (X)

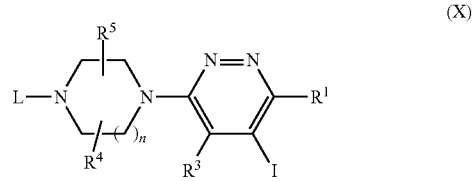

(X)

where $R^1$ is trifluoromethyl and $R^3$, $R^4$, $R^5$ and n are as defined before and L represents a suitable protecting group, such as tert-butyloxycarbonyl, with a corresponding arylboronic acid $R^2$—$B(OH)_2$ in the presence of a suitable catalyst such as 1,1'-bis(diphenylphosphino)ferrocenepalladium(II).dichloride, dichloromethane in the presence of suitable ligand such as 1,1'-bis(diphenylphosphino)ferrocene and a base such as potassium phosphate in a suitable inert solvent such as dioxane at an elevated temperature.

Compounds of Formula (X) wherein $R^1$ is trifluoromethyl and $R^3$, $R^4$, $R^5$ and n are as defined before and L represents a suitable protecting group, such as tert-butyloxycarbonyl, may be prepared by reacting a compound of Formula (XI)

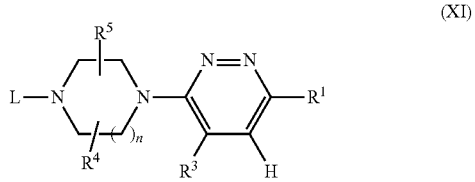

(XI)

where $R^1$ is trifluoromethyl, and, $R^3$, $R^4$, $R^5$ and n are as defined before and L represents a suitable protecting group, such as tert-butyloxycarbonyl, with iodine in the presence of a suitable base such as a mixture of buthyllithium and 2,2,6,6-tetramethylpiperidine in a suitable inert solvent such as tetrahydrofuran at low temperatures, typically ranging from −78° C. to 0° C.

Compounds of Formula (XI) wherein $R^1$ is trifluoromethyl, $R^3$, $R^4$, $R^5$ and n are as defined before and L represents a suitable protecting group, such as tert-butyloxycarbonyl, may be prepared by reacting 6-chloro-3-trifluoromethylpyridazine (prepared by following the procedure described in Goodman, A. J.; Stanforth, S. P; Tarbit B. Tetrahedron 1999, 55, 15067-15070) with tert-butyl 1-piperazinecarboxylate in the presence of a suitable base such as diisopropylethylamine in a suitable solvent such as acetonitrile at a convenient temperature, either by conventional heating or under microwave irradiation for a period of time to ensure the completion of the reaction.

Compounds of Formula (I-c) wherein $R^{6'}$ is $R^6$ as defined before but not hydrogen, $R^1$ is trifluoromethyl, $R^3$, $R^4$, $R^5$, $R^7$ and n are as defined before,

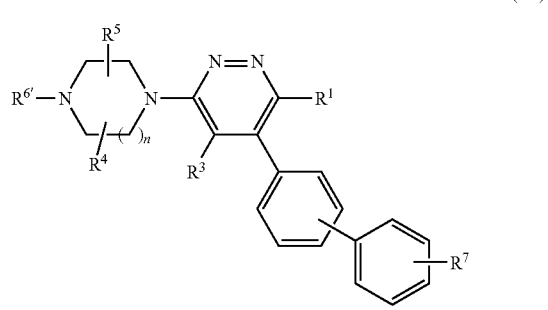

(I-c)

can be prepared by reacting a compound of Formula (I-d)

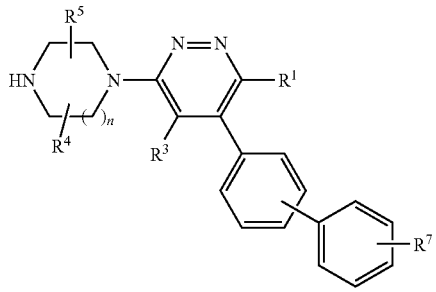
(I-d)

wherein $R^1$ is trifluoromethyl, $R^3$, $R^4$, $R^5$, $R^7$ and n are as defined before, with a reagent of Formula $R^{6'}$—W wherein $R^{6'}$ is $R^6$ as defined before but not hydrogen and W represents a leaving group such as halo, e.g. chloro, bromo or iodo, or a sulfonyloxy group, e.g. methylsulfonyloxy, trifluoromethylsulfonyloxy or methylphenylsulfonyloxy in the presence of a base such as diisopropylethylamine, in a suitable solvent such as acetonitrile and under suitable reaction conditions, such as a convenient temperature, either by conventional heating or under microwave irradiation for a period of time to ensure the completion of the reaction.

Alternatively, the compounds of Formula (I-c) wherein $R^{6'}$ is $R^6$ as defined before but not hydrogen, $R^1$ is trifluoromethyl, $R^3$, $R^4$, $R^5$, $R^7$ and n are as defined before, can be prepared from a compound of Formula (I-d) wherein $R^1$ is trifluoromethyl, $R^3$, $R^4$, $R^5$, $R^7$ and n are as defined before, by reductive N-alkylation with an appropriate ketone or aldehyde in the presence of a suitable reducing agent such as sodium triacetoxyborohydride in a suitable solvent such as tetrahydrofuran.

Compounds of Formula (I-d) wherein $R^1$ is trifluoromethyl, $R^3$, $R^4$, $R^5$, $R^7$ and n are as defined before, may be prepared by deprotection of the protecting group in an intermediate of Formula (XII)

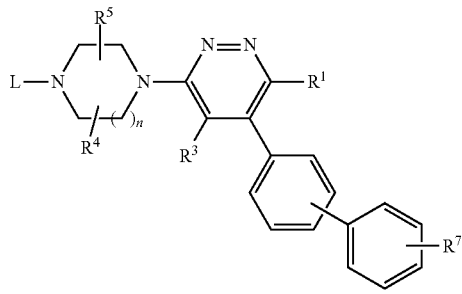
(XII)

where $R^1$ is trifluoromethyl, $R^3$, $R^4$, $R^5$, $R^7$ and n are as defined before and L represents a suitable protecting group, such as tert-butyloxycarbonyl, under suitable conditions, such as trifluoroacetic acid in dichloromethane or Amberlyst® 15 ion exchange resin, acidic form in methanol when L represents a tert-butyloxycarbonyl group.

Compounds of Formula (XII) wherein $R^1$ is trifluoromethyl, $R^3$, $R^4$, $R^5$, $R^7$ and n are as defined before and L represents a suitable protecting group, such as tert-butyloxycarbonyl can be prepared by reacting a compound of Formula (XIII)

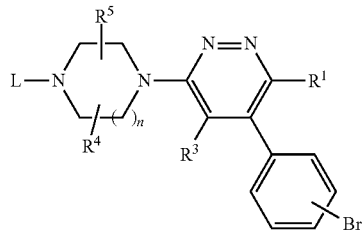
(XIII)

wherein $R^1$ is trifluoromethyl, $R^3$, $R^4$, $R^5$ and n are as defined before and L represents a suitable protecting group, such as tert-butyloxycarbonyl, with a corresponding arylboronic acid in the presence of a suitable catalyst such as trans-Pd(OAc)$_2$(Cy$_2$NH)$_2$ (prepared by following the procedure described in Tao, B.; Boykin, D. W. Tetrahedron Lett. 2003, 44, 7993-7996) in the presence of suitable base such as potassium phosphate in a suitable inert solvent such as dioxane, under suitable reaction conditions, such as a convenient temperature, either by conventional heating or under microwave irradiation for a period of time to ensure the completion of the reaction.

Compounds of Formula (I) wherein $R^1$ is cyano, $R^6$ is as defined before but not hydrogen, $R^2$, $R^3$, $R^4$, $R^5$ and n are as described before, can be prepared by reacting a compound of Formula (I-e)

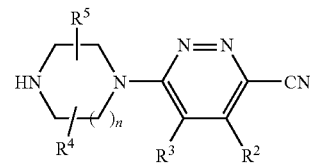
(I-c)

wherein and $R^2$, $R^3$, $R^4$, $R^5$ and n are as described before, with a reagent of Formula $R^{6'}$—W wherein $R^{6'}$ is $R^6$ as defined before but not hydrogen and W represents a leaving group such as halo, e.g. chloro, bromo or iodo, or a sulfonyloxy group, e.g. methylsulfonyloxy, trifluoromethylsulfonyloxy or methylphenylsulfonyloxy in the presence of a base such as diisopropylethylamine, in a suitable solvent such as acetonitrile and under suitable reaction conditions, such as a convenient temperature, either by conventional heating or under microwave irradiation for a period of time to ensure the completion of the reaction.

Alternatively, the compounds of Formula (I) wherein $R^1$ is cyano, $R^{6'}$ is $R^6$ but other than hydrogen, and $R^2$, $R^3$, $R^4$, $R^5$ and n are as described before, can be prepared from a compound of Formula (I-e) wherein $R^1$ is cyano, $R^{6'}$ is hydrogen, and $R^2$, $R^3$, $R^4$, $R^5$ and n are as described before, by reductive N-alkylation with an appropriate ketone or aldehyde in the presence of a suitable reducing agent in a suitable solvent.

Compounds of Formula (I) wherein $R^1$ is cyano, $R^6$ is as defined before, and $R^2$, $R^3$, $R^4$, $R^5$ and n are as described before, may be prepared by deprotection of the protecting group in an intermediate of Formula (XIV)

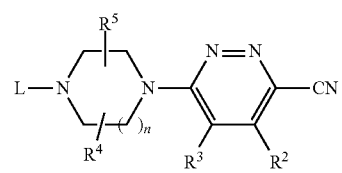
(XIV)

where $R^2$, $R^3$, $R^4$, $R^5$ and n are as described before and L represents a suitable protecting group, such as tert-butyloxycarbonyl, under suitable conditions, such as trifluoroacetic acid in dichloromethane or Amberlyst® 15 ion exchange resin, acidic form in methanol when L represents a tert-butyloxycarbonyl group.

Compounds of Formula (XIV) wherein $R^2$, $R^3$, $R^4$, $R^5$ and n are as described before and L represents a suitable protecting group, such as tert-butyloxycarbonyl, were prepared by reacting a compound of Formula (VIII) wherein $R^1$ is chloro, and $R^2$, $R^3$, $R^4$, $R^5$ and n are as described before and L represents a suitable protecting group, such as tert-butyloxycarbonyl, with zinc cyanide in the presence of a suitable catalyst, such as tetrakis(triphenylphosphine)palladium (0) in a suitable solvent, such as N,N-dimethylformamide under suitable reaction conditions, such as a convenient temperature, either by conventional heating or under microwave irradiation for a period of time to ensure the completion of the reaction.

Experimental Part

Chemistry

Microwave assisted reactions were performed in a single-mode reactor: Emrys™ Optimizer microwave reactor (Personal Chemistry A.B., currently Biotage).

Final purification of Examples (E1-E 39) was carried out either by column chromatography on silica gel using the eluent described or by reversed phase preparative HPLC on a Hyperprep RP 18 BDS (Shandon) (8 µm, 200 mm, 250 g) column. Three mobile phases (mobile phase A: 90% 0.5% ammoniumacetate+10% acetonitrile; mobile phase B: methanol; mobile phase C: acetonitrile) were used to run a gradient method starting with 75% A and 25% B with a flow rate of 40 ml/min, hold for 0.5 minutes at the same conditions followed with an increase of the flow rate to 80 ml/min in 0.01 minutes to 50% B and 50% C in 41 minutes, to 100% C in 20 minutes and hold these conditions for 4 minutes.

$^1$H spectra were recorded on a Bruker DPX 360, DPX 400 or a Bruker AV-500 spectrometer. The chemical shifts are expressed in ppm relative to tetramethylsilane.

Melting point determination was performed on a Mettler FP62 apparatus.

LCMS

General LCMS Method A:

The HPLC measurement was performed using a HP 1100 from Agilent Technologies comprising a quaternary pump with degasser, an autosampler, a column oven (set at 40° C. except for Method 4 where the temperature was set at 60° C.), a diode-array detector (DAD) and a column as specified in the respective methods below. Flow from the column was split to a MS detector. The MS detector was configured with an electrospray ionization source. Nitrogen was used as the nebulizer gas. The source temperature was maintained at 140° C. Data acquisition was performed with MassLynx-Openlynx software.

General LCMS Method B:

The HPLC measurement was performed using an Agilent 1100 module comprising a pump, a diode-array detector (DAD) (wavelength used 220 nm), a column heater and a column as specified in the respective methods below. Flow from the column was split to a Agilent MSD Series G1946C and G1956A. MS detector was configured with API-ES (atmospheric pressure electrospray ionization). Mass spectra were acquired by scanning from 100 to 1000. The capillary needle voltage was 2500 V for positive ionization mode and 3000 V for negative ionization mode. Fragmentation voltage was 50V. Drying gas temperature was maintained at 350° C. at a flow of 10 l/min.

LCMS Method 1

In addition to general LCMS method A: Reversed phase HPLC was carried out on an ACE-C18 column (3.0 µm, 4.6×30 mm) from Advanced Chromatography Technologies, with a flow rate of 1.5 ml/min. The gradient conditions used are: 80% A (0.5 g/l ammonium acetate solution), 10% B (acetonitrile), 10% C (methanol) to 50% B and 50% C in 6.5 minutes, to 100% B at 7 minutes and equilibrated to initial conditions at 7.5 minutes until 9.0 minutes. Injection volume 5 µl. High-resolution mass spectra (Time of Flight, TOF) were acquired only in positive ionization mode by scanning from 100 to 750 in 0.5 seconds using a dwell time of 0.1 seconds. The capillary needle voltage was 2.5 kV for positive ionization mode and the cone voltage was 20 V. Leucine-Enkephaline was the standard substance used for the lock mass calibration.

LCMS Method 2

In addition to general LCMS method A: Reversed phase HPLC was carried out on an ACE-C18 column (3.0 µm, 4.6×30 mm) from Advanced Chromatography Technologies, with a flow rate of 1.5 ml/min. The gradient conditions used are: 80% A (0.5 g/l ammonium acetate solution), 10% B (acetonitrile), 10% C (methanol) to 50% B and 50% C in 6.5 minutes, to 100% B at 7 minutes and equilibrated to initial conditions at 7.5 minutes until 9.0 minutes. Injection volume 5 µl. High-resolution mass spectra (Time of Flight, TOF) were acquired by scanning from 100 to 750 in 0.5 seconds using a dwell time of 0.3 seconds. The capillary needle voltage was 2.5 kV for positive ionization mode and 2.9 kV for negative ionization mode. The cone voltage was 20 V for both positive and negative ionization modes. Leucine-Enkephaline was the standard substance used for the lock mass calibration.

LCMS Method 3

Same as LCMS Method 1 using 10 µl of injection volume.

LCMS Method 4

In addition to general LCMS method A: Reversed phase HPLC was carried out on an XDB-C18 cartridge (1.8 µm, 2.1×30 mm) from Agilent, with a flow rate of 1 ml/min. The gradient conditions used are: 90% A (0.5 g/l ammonium acetate solution), 5% B (acetonitrile), 5% C (methanol) to 50% B and 50% C in 6.5 minutes, to 100% B at 7.0 minutes and equilibrated to initial conditions at 7.5 minutes until 9.0 minutes. Injection volume 2 µl. High-resolution mass spectra (Time of Flight, TOF) were acquired only in positive ionization mode by scanning from 100 to 750 in 0.5 seconds using a dwell time of 0.1 seconds. The capillary needle voltage was 2.5 kV and the cone voltage was 20 V. Leucine-Enkephaline was the standard substance used for the lock mass calibration.

LCMS Method 5

In addition to general LCMS method A: Reversed phase HPLC was carried out on an ACE-C18 column (3.0 µm, 4.6×30 mm) from Advanced Chromatography Technologies, with a flow rate of 1.5 ml/min. The gradient conditions used are: 80% A (1 g/l ammonium bicarbonate solution), 10% B (acetonitrile), 10% C (methanol) to 50% B and 50% C in 6.5 minutes, to 100% B at 7 minutes and equilibrated to initial conditions at 7.5 minutes until 9.0 minutes. Injection volume 5 µl. High-resolution mass spectra (Time of Flight, TOF) were acquired only in positive ionization mode by scanning from 100 to 750 in 0.5 seconds using a dwell time of 0.1 seconds. The capillary needle voltage was 2.5 kV for positive ionization mode and the cone voltage was 20 V. Leucine-Enkephaline was the standard substance used for the lock mass calibration.

LCMS Method 6

In addition to general LCMS method B: Reversed phase HPLC was carried out on a YMC-Pack ODS-AQ, 50×2.0 mm 5 µm column with a flow rate of 0.8 ml/min. Two mobile phases (mobile phase A: water with 0.1% TFA; mobile phase B: acetonitrile with 0.05% TFA) were used. First, 100% A was held for 1 minute. Then a gradient was applied to 40% A and 60% B in 4 minutes and held for 2.5 minutes. Typical injection volumes of 2 µl were used. Oven temperature was 50° C. (MS polarity: positive)

LCMS Method 7

In addition to general LCMS method B: Reversed phase HPLC was carried out on a YMC-Pack ODS-AQ, 50×2.0 mm 5 µm column with a flow rate of 0.8 ml/min. Two mobile phases (mobile phase A: water with 0.1% TFA; mobile phase B: acetonitrile with 0.05% TFA) were used. First, 90% A and 10% B was held for 0.8 minutes. Then a gradient was applied to 20% A and 80% B in 3.7 minutes and held for 3 minutes. Typical injection volumes of 2 µl were used. Oven temperature was 50° C. (MS polarity: positive)

Description 1

5,5,5-Trifluoro-4-oxo-3-phenyl-pent-2-enoic acid (D1)

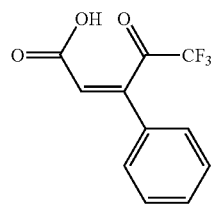 [SMILES: O=C(O)/C=C(\C(=O)C(F)(F)F)c1ccccc1]

To a stirred solution of phenylmaleic anhydride (18.7 g, 0.107 mol) in acetonitrile (180 ml) at 0° C. (ice/water/sodium chloride bath—temperature of the bath −10° C.), was added CsF (18.6 g, 0.127 mol), followed by the drop-wise addition of $CF_3SiMe_3$ (18.58 ml, 0.127 mol), under nitrogen. The reaction mixture was stirred for 1 h, and was then diluted with diethyl ether and extracted with 2M sodium hydroxide (200 ml). The separated aqueous layer was acidified to pH=1 by the addition of conc. hydrochloric acid. This mixture was extracted with dichloromethane. The separated organic layer was dried ($Na_2SO_4$), and the solvent was evaporated in vacuo to yield D1 (22.6 g, 86%) as a mixture of isomers (80/11 ratio by LCMS). $C_{11}H_7F_3O_3$ requires 244; Found 243 (M-H)⁻.

Description 2

5-Phenyl-6-trifluoromethyl-2H-pyridazine-3-one (D2)

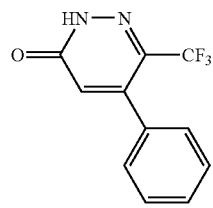 [SMILES: O=c1cc(-c2ccccc2)c(C(F)(F)F)n[nH]1]

To a stirred solution of 5,5,5-trifluoro-4-oxo-3-phenyl-pent-2-enoic acid (D1) (22.6 g, 0.084 mol) in a mixture of acetonitrile (150 ml) and acetic acid (15 ml), was added hydrazine hydrate (7.75 ml, 0.148 mol). The reaction mixture was heated at reflux for 16 h, cooled to room temperature, diluted with dichloromethane and then extracted with 0.5 M hydrochloric acid (150 ml). The organic layer was separated, dried ($Na_2SO_4$) and the solvent evaporated in vacuo to yield D2 (20.7 g, 100%) as a mixture of isomers (75/5 ratio by LCMS). $C_{11}H_7F_3N_2O$ requires 240; Found 239 (M-H)⁻.

Description 3

6-Chloro-4-phenyl-3-trifluoromethyl-pyridazine (D3)

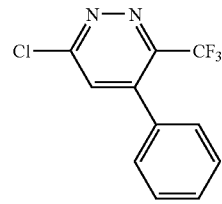 [SMILES: FC(F)(F)c1nnc(Cl)cc1-c1ccccc1]

To a stirred solution of 5-phenyl-6-trifluoromethyl-2H-pyridazine-3-one (D2) (20.66 g, 0.086 mol) in acetonitrile (150 ml) was added phosphorous oxychloride (20 ml, 0.215 mmol) and the reaction heated at reflux for 1 h. After this period, the reaction mixture was poured into a saturated solution of sodium hydrogen carbonate, ice and dichloromethane. Further solid sodium hydrogen carbonate was then added until gas evolution had ceased. The organic layer was then separated, dried ($Na_2SO_4$) and the solvents evaporated in vacuo. The crude residue was then filtered through silica gel, eluting with dichloromethane, in order to remove the minor isomer. After evaporation of the solvent, the crude product was then re-purified by column chromatography (silica; 0-25% ethyl acetate/heptane) to yield D3 (7.1 g, 32%). $C_{11}H_6ClF_3N_2$ requires 258; Found 259 (MH⁺).

Description 4

4-(5-Phenyl-6-trifluoromethyl-pyridazin-3-yl)-piperazine-1-carboxylic acid tert-butyl ester (D4)

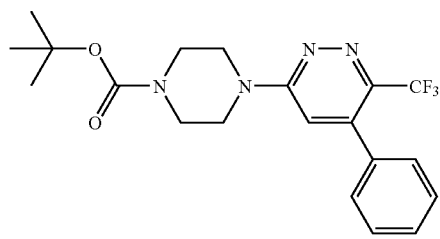

To a stirred solution of 6-chloro-4-phenyl-3-trifluoromethyl-pyridazine (D3) (7.1 g, 0.0274 mol) and N-Boc-piperazine (5.62 g, 0.0302 mol) in acetonitrile (150 ml) was added diisopropylethylamine (5.1 ml, 0.0302 mol) and the mixture heated at 150° C. for 20 min., under microwave irradiation. After this period, the reaction mixture was diluted with dichloromethane and extracted with water. The organic layer was separated, dried (MgSO$_4$) and the solvents evaporated in vacuo. The crude product was purified by column chromatography (silica; 20% ethyl acetate in heptane, followed by 10% ethyl acetate in dichloromethane). After evaporation of the solvent, the crude product was crystallised from heptane to yield D4 (10.4 g, 93%). C$_{20}$H$_{23}$F$_3$N$_4$O$_2$ requires 408; Found 409 (MH$^+$).

Description 5

5,5,5-Trifluoro-3-(4-fluorophenyl)-4-oxo-pent-2-enoic acid (D5)

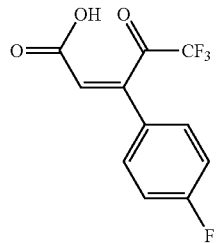 [SMILES: O=C(O)/C=C(\C(=O)C(F)(F)F)c1ccc(F)cc1]

To a stirred solution of 4-fluorophenylmaleic anhydride (1.42 g, 7.39 mmol) (prepared by procedures similar to those described in Dean, W. D.; Bum, D. M. J. Org. Chem. 1993, 58, 7916-7917), in acetonitrile (15 ml) at 0° C. (ice/water/sodium chloride bath—temperature of the bath –10° C.), was added CsF (1.1 g, 7.39 mmol), followed by the drop-wise addition of CF$_3$SiMe$_3$ (1 ml, 7.39 mmol), under nitrogen. The reaction mixture was stirred for 1 h, and then diluted with diethyl ether and extracted with 2M sodium hydroxide (200 ml). The organic layer was removed and the aqueous layer acidified to pH=1 by the addition of conc. hydrochloric acid. The mixture was extracted with dichloromethane and the organic layer removed, dried (Na$_2$SO$_4$), and the solvent evaporated in vacuo to yield D5 (1.4 g, 72%) as a mixture of isomers. C$_{11}$H$_6$F$_4$O$_3$ requires 262 Found 261 (M-H)$^-$.

Description 6

5-(4-Fluorophenyl)-6-trifluoromethyl-2H-pyridazine-3-one (D6)

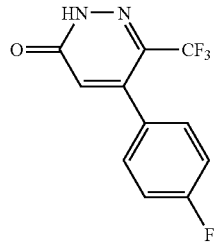 [SMILES: O=c1cc(-c2ccc(F)cc2)c(C(F)(F)F)n[nH]1]

To a stirred solution of 5,5,5-trifluoro-3-(4-fluorophenyl)-4-oxo-pent-2-enoic acid (D5) (1.4 g, 5.3 mmol) in a mixture of ethanol (10 ml) and acetic acid (1 ml), was added hydrazine hydrate (0.49 ml, 9.33 mmol). The reaction mixture was heated at reflux for 16 h, cooled to room temperature, diluted with dichloromethane and then extracted with 0.5 M hydrochloric acid (150 ml). The organic layer was separated, dried (Na$_2$SO$_4$) and the solvent evaporated in vacuo to yield D6 (0.96 g, 70%) as a mixture of isomers. C$_{11}$H$_6$F$_4$N$_2$O requires 258; Found 259 (MH$^+$).

Description 7

6-Chloro-4-(4-fluorophenyl)-3-trifluoromethyl-pyridazine (D7)

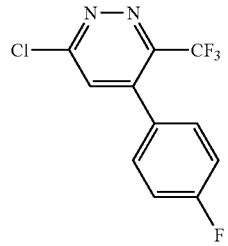 [SMILES: Fc1ccc(-c2cc(Cl)nnc2C(F)(F)F)cc1]

To a stirred solution of 5-(4-fluorophenyl)-6-trifluoromethyl-2H-pyridazine-3-one (D6) (0.96 g, 3.7 mmol) in acetonitrile (10 ml) was added phosphorous oxychloride (0.866 ml, 9.3 mmol) and the reaction was stirred at 180° C. for 30 min., under microwave irradiation. After this period, the reaction mixture was poured into a saturated solution of sodium hydrogen carbonate, ice and dichloromethane. Further solid sodium hydrogen carbonate was then added until gas evolution had ceased. The organic layer was then separated, dried (Na$_2$SO$_4$) and the solvents evaporated in vacuo to yield D7 (0.81 g, 79%). Only traces of the undesired isomer were detected after work-up. C$_{11}$H$_5$ClF$_4$N$_2$ requires 276; Found 277 (MH$^+$).

Description 8

4-[5-(4-Fluorophenyl)-6-trifluoromethyl-pyridazin-3-yl]-piperazine-1-carboxylic acid tert-butyl ester (D8)

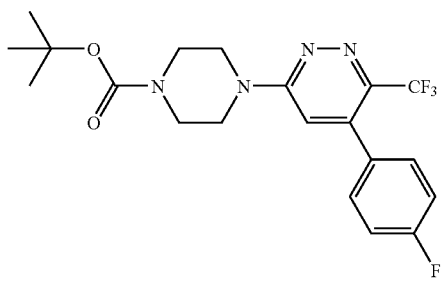 [SMILES: CC(C)(C)OC(=O)N1CCN(c2cc(-c3ccc(F)cc3)c(C(F)(F)F)nn2)CC1]

To a stirred solution of 6-chloro-4-(4-fluorophenyl)-3-trifluoromethyl-pyridazine (D7) (0.81 g, 2.93 mmol) and N-Boc-piperazine (0.818 g, 4.39 mmol) in acetonitrile (10 ml) was added diisopropylethylamine (1 ml, 5.9 mmol) and the mixture was stirred at 80° C. for 30 min., under microwave irradiation. After this period, the reaction mixture was diluted with dichloromethane and extracted with water. The organic layer was separated, dried (MgSO$_4$) and the solvents evaporated in vacuo to yield D8 (1.27 g, 62%) $C_{20}H_{22}F_4N_4O_2$ requires 426; Found 427 (MH+).

Description 9

4-(6-Trifluoromethyl-pyridazin-3-yl)-piperazine-1-carboxylic acid tert-butyl ester (D9)

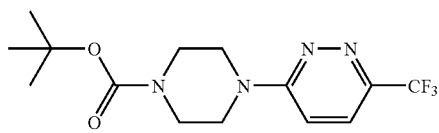 [SMILES: CC(C)(C)OC(=O)N1CCN(c2ccc(C(F)(F)F)nn2)CC1]

A mixture of 6-chloro-3-trifluoromethylpyridazine (0.666 g, 5.09 mmol) (prepared by following the procedure described in Goodman, A. J.; Stanforth, S. P; Tarbit B. Tetrahedron 1999, 55, 15067-15070), N-Boc-piperazine (1.138 g, 6.11 mmol) and diisopropylethylamine (1.95 ml, 1.12 mmol) in acetonitrile (10 ml) was stirred at 180° C. for 30 min., under microwave irradiation. The solvent was evaporated in vacuo and the residue was purified by column chromatography (silica gel; hexane/ethyl acetate) to yield D9 (1.67 g, 99%) as a light yellow solid. $C_{14}H_{19}F_3N_4O_2$ requires 332; Found 333 (MH+).

Description 10

4-(5-Iodo-6-trifluoromethyl-pyridazin-3-yl)-piperazine-1-carboxylic acid tert-butyl ester (D10)

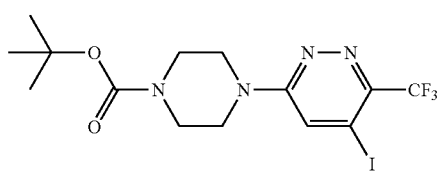 [SMILES: CC(C)(C)OC(=O)N1CCN(c2cc(I)c(C(F)(F)F)nn2)CC1]

To a mixture of butyllithium (2.5 M in hexanes) (6.31 ml, 15.79 mmol) in tetrahydrofuran (125 ml) at 0° C., was added 2,2,6,6-tetramethylpiperidine (3.808 ml, 22.56 mmol). The reaction mixture was then stirred at room temperature for 1 h. The mixture was cooled to −78° C. and then a solution of 4-(6-trifluoromethyl-pyridazin-3-yl)-piperazine-1-carboxylic acid tert-butyl ester (D9) (2.5 g, 7.52 mmol) in tetrahydrofuran (20 ml) was added. The mixture was stirred for 1 h. at −78° C. before adding a solution of iodine (2.29 g, 9.024 mmol) in tetrahydrofuran (10 ml). The mixture was stirred at −78° C. for 1 h. and then diluted with a 10% solution of acetic acid in tetrahydrofuran. The mixture was then allowed to reach room temperature and then the solvent was evaporated in vacuo. The residue was diluted with dichloromethane and extracted with water. The organic layer was separated, dried (MgSO4), filtered and the solvent evaporated in vacuo. The residue was precipitated from diethyl ether to yield D10 (2.81 g, 82%) as a light yellow solid. $C_{14}H_{18}F_3IN_4O_2$ requires 458; Found 459 (MH+).

Description 11

4-[5-(2-Tolyl)-6-trifluoromethyl-pyridazin-3-yl]-piperazine-1-carboxylic acid tert-butyl ester (D11)

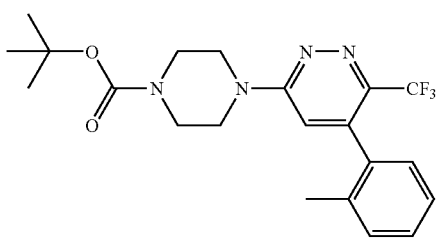 [SMILES: Cc1ccccc1-c1cc(N2CCN(C(=O)OC(C)(C)C)CC2)nnc1C(F)(F)F]

A mixture of 4-(5-iodo-6-trifluoromethyl-pyridazin-3-yl)-piperazine-1-carboxylic acid tert-butyl ester (D10) (0.20 g, 0.436 mmol), o-tolylboronic acid (0.071 g, 0.523 mmol), 1,1'-bis(diphenylphosphino)ferrocenepalladium(II).dichloride, dichloromethane (0.022 g, 0.026 mmol), 1,1'-bis(diphenylphosphino)ferrocene (0.015 g, 0.026 mmol) and potassium phosphate (0.138 g, 0.654 mmol) in dioxane (8.5 ml) was stirred at 80° C. for 16 h. and then at 110° C. for 2 days. The mixture was then filtered through a pad of diatomaceous earth and the solvent was evaporated in vacuo. The residue was purified by column chromatography (silica gel; dichloromethane/methanol 70/30) to yield D11 (0.089 g, 48%) as a yellow solid. $C_{21}H_{25}F_3N_4O_2$ requires 422; Found 423 (MH+).

Description 12

4-[5-(4'-Fluorobiphenyl-4-yl)-6-trifluoromethyl-pyridazin-3-yl]-piperazine-1-carboxylic acid tert-butyl ester (D12)

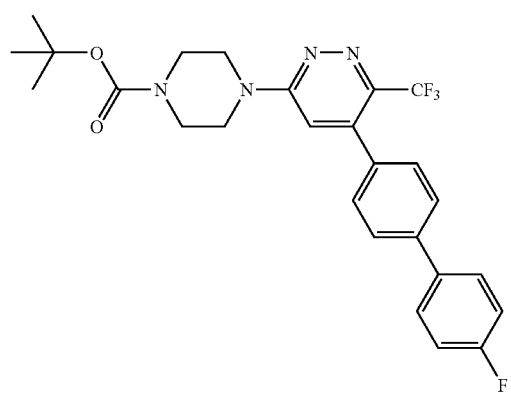 [SMILES: CC(C)(C)OC(=O)N1CCN(c2cc(-c3ccc(-c4ccc(F)cc4)cc3)c(C(F)(F)F)nn2)CC1]

A mixture of 4-[5-(4-bromophenyl)-6-trifluoromethyl-pyridazin-3-yl]-piperazine-1-carboxylic acid tert-butyl ester (0.2 g, 0.41 mmol) (prepared by procedures similar to those described for D8), 4-fluorobenzeneboronic acid (0.069 g, 0.49 mmol), trans-Pd(OAc)2(Cy2NH)2 (0.015 g, 0.026 mmol), prepared by following the procedure described in Tao, B.; Boykin, D. W. Tetrahedron Lett. 2003, 44, 7993-

7996, and potassium phosphate (0.261 g, 1.23 mmol) in dioxane (3 ml) was stirred at 80° C. overnight. The reaction mixture was then diluted with dichloromethane and extracted with a saturated solution of sodium carbonate. The organic layers were separated, dried (Na$_2$SO$_4$), filtered and the solvent evaporated in vacuo. The residue was then purified by column chromatography (silica gel; dichloromethane/heptane 3:7 to 10:0). The desired fractions were collected and evaporated in vacuo to yield D12 (0.115 g, 56%). C$_{26}$H$_{26}$F$_4$N$_4$O$_2$ requires 502; Found 503 (MH$^+$).

Description 13

4-(6-Chloro-5-phenyl-pyridazin-3-yl)-piperazine-1-carboxylic acid tert-butyl ester (D13)

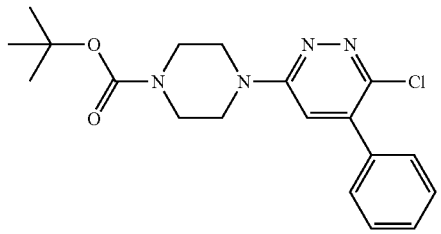 [SMILES: CC(C)(C)OC(=O)N1CCN(c2cc(-c3ccccc3)c(Cl)nn2)CC1]

A mixture of 3,6-dichloro-4-phenyl-pyridazine (0.41 g, 1.82 mmol), prepared by following the procedure described in WO-2005/013907, N-Boc-piperazine (0.509 g, 2.73 mmol) and diisopropylethylamine (0.634 ml, 3.64 mmol) in acetonitrile (7.5 ml) was stirred at 180° C. for 40 min., under microwave irradiation, and then for a further 30 min. After this period, additional amounts of diisopropylethylamine (0.1 ml, 0.57 mmol) and N-Boc-piperazine (0.1 g, 0.54 mmol) were added and the resulting mixture was stirred at 180° C. for 40 min. The solvent was evaporated in vacuo and then, dichloromethane and a saturated solution of ammonium chloride were added. The organic layer was separated, dried (Na$_2$SO$_4$), filtered and the solvent evaporated in vacuo. The residue was then purified by column chromatography (silica gel; dichloromethane and heptane/ethyl acetate 8:2 to 7:3). The desired fractions were collected and evaporated in vacuo to yield D13 (0.137 g, 20%) as a white solid. C$_{19}$H$_{23}$ClN$_4$O$_2$ requires 374; Found 375 (MH$^+$).

Description 14

4-(6-Cyano-5-phenyl-pyridazin-3-yl)-piperazine-1-carboxylic acid tert-butyl ester (D14)

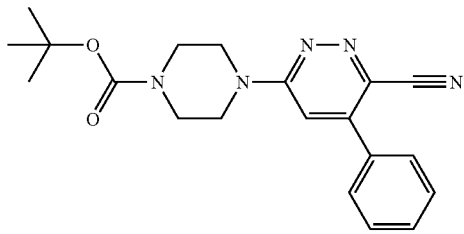 [SMILES: CC(C)(C)OC(=O)N1CCN(c2cc(-c3ccccc3)c(C#N)nn2)CC1]

To a mixture of zinc cyanide (0.077 g, 0.66 mmol) and tetrakis(triphenylphosphine)palladium (0) (0.1 g, 0.09 mmol) was added a solution of 4-(6-chloro-5-phenyl-pyridazin-3-yl)-piperazine-1-carboxylic acid tert-butyl ester (D13) (0.137 g, 0.36 mmol) in N,N-dimethylformamide (3.5 ml). The resulting mixture was stirred at 160° C. for 30 min, under microwave irradiation. The solvent was evaporated in vacuo to yield D14 (0.133 g, quant.). C$_{20}$H$_{23}$N$_5$O$_2$ requires 365; Found 366 (MH$^+$).

Description 15

4-[5-(5-Chloro-thiophen-2-yl)-6-trifluoromethyl-pyridazin-3-yl]-piperazine-1-carboxylic acid tert-butyl ester (D15)

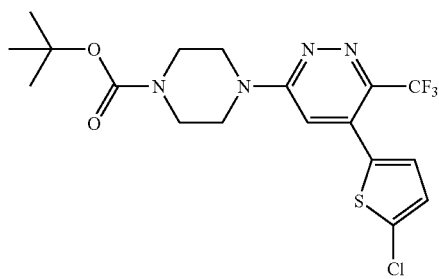 [SMILES: CC(C)(C)OC(=O)N1CCN(c2cc(-c3ccc(Cl)s3)c(C(F)(F)F)nn2)CC1]

A mixture of 4-(5-iodo-6-trifluoromethyl-pyridazin-3-yl)-piperazine-1-carboxylic acid tert-butyl ester (D10) (0.20 g, 0.436 mmol), 5-chlorothiophene-2-boronic acid (0.082 g, 0.51 mmol), tetrakis(triphenylphosphine)palladium (0) (0.024 g, 0.021 mmol) and sodium carbonate (0.103 g, 0.96 mmol) in dimethoxyethane (3 ml) and water (0.75 ml) was stirred in a sealed tube at 110° C. for 16 h. The mixture was then filtered through a pad of diatomaceous earth and the solvent was evaporated in vacuo. The residue was purified by column chromatography (silica gel; dichloromethane/10% ammonia in methanol (7M) in dichloromethane 97/3) to yield D15 (0.152 g, 67%) as a yellow syrup. C$_{18}$H$_{20}$ClF$_3$N$_4$O$_2$S requires 448; Found 449 (MH$^+$).

Example 1

4-Phenyl-6-piperazin-1-yl-3-trifluoromethyl-pyridazine (E1)

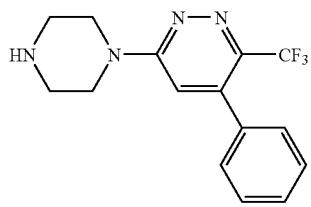

To a solution of 4-(5-phenyl-6-trifluoromethyl-pyridazin-3-yl)-piperazine-1-carboxylic acid tert-butyl ester (D4) (1.8 g, 0.0044 mol) in methanol (125 ml) was added Amberlyst® 15 ion exchange resin, acidic form (4.1 mmol/g) (5.3 g, 0.022 mol) and the reaction mixture was shaken at room temperature for 18 h. After this period, the mixture was filtered and then a saturated solution of ammonia in methanol was added. The mixture was shaken for 1 h, filtered and the filtrate evaporated in vacuo. The crude product was crystallised from ether/heptane to yield E1 (1.3 g, 96%). C$_{15}$H$_{15}$F$_3$N$_4$ requires 308; Found 309 (MH$^+$).

Melting point (ether/heptane): 130.7° C.

$^1$H NMR (500 MHz, chloroform-d) δ ppm: 1.71 (bs, 1H), 3.01 (t, J=5.20 Hz, 4H), 3.77 (t, J=5.20 Hz, 4H), 6.71 (s, 1H), 7.29-7.37 (m, 2H), 7.42-7.49 (m, 3H).

$^{13}$C NMR (126 MHz, chloroform-d) δ ppm: 45.72 (s, 2 CH$_2$), 45.76 (s, 2 CH$_2$), 112.73 (s, CH), 122.48 (q, J=581 Hz, C), 128.19 (s, CH), 128.36 (s, 2 CH), 129.01 (s, CH), 135.66 (s, C), 140.55 (s, C), 141.03 (s, C), 160.22 (s, C).

Example 2

6-(4-Ethylpiperazin-1-yl)-4-phenyl-3-trifluoromethyl-pyridazine (E2)

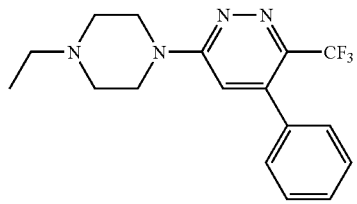 [SMILES: CCN1CCN(c2cc(-c3ccccc3)c(C(F)(F)F)nn2)CC1]

To a mixture of 4-phenyl-6-piperazin-1-yl-3-trifluoromethyl-pyridazine (E1) (0.15 g, 0.49 mmol) in tetrahydrofuran (5 ml), was added acetaldehyde (55 ml, 0.97 mmol). The reaction mixture was stirred at room temperature for 30 min., and then sodium triacetoxyborohydride (0.154 g, 0.73 mmol) was added. The reaction mixture was stirred at room temperature for 16 h. Then, more acetaldehyde (55 ml, 0.97 mmol) and sodium triacetoxyborohydride (0.154 g, 0.73 mmol) were added and the mixture was stirred at room temperature for 4 h. Dichloromethane was then added and the mixture was extracted with a saturated solution of ammonium chloride. The organic phase was separated, dried (Na$_2$SO$_4$), filtered and the solvent evaporated in vacuo. The residue was purified by column chromatography (silica gel; ethyl acetate/10% ammonia in methanol (7M) in dichloromethane 10:0 to 8:2). The desired fractions were collected, the solvent evaporated in vacuo, the residue dissolved in acetonitrile and converted into its hydrochloric acid salt by addition of a saturated solution of hydrochloric acid in diethyl ether. The white solid obtained was filtered and dried affording E2 (0.039 g, 21%). C$_{17}$H$_{19}$F$_3$N$_4$.HCl; free base requires 336; Found 337 (MH$^+$).

Melting point: 281.9° C.

$^1$H NMR (500 MHz, DMSO-d$_6$) δ ppm: 1.28 (t, J=7.22 Hz, 3H), 2.98-3.22 (m, 4H), 3.48-3.64 (m, 4H), 4.73 (d, J=13.58 Hz, 2H), 7.32-7.46 (m, 3H), 7.46-7.60 (m, 3H), 11.26 (br. s., 1H).

Example 3

6-[4-(3,5-Difluorobenzyl)piperazin-1-yl]-4-phenyl-3-trifluoromethyl-pyridazine (E3)

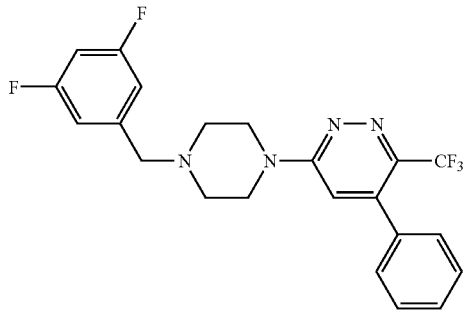 [SMILES: Fc1cc(F)cc(CN2CCN(c3cc(-c4ccccc4)c(C(F)(F)F)nn3)CC2)c1]

A mixture of 4-phenyl-6-piperazin-1-yl-3-trifluoromethyl-pyridazine (E1) (0.050 g, 0.16 mmol), 3,5-difluorobenzyl bromide (0.031 ml, 0.24 mmol) and diisopropylethylamine (0.056 ml, 0.32 mmol) in acetonitrile (2 ml) was stirred at 100° C. for 10 min., under microwave irradiation. The solvent was evaporated in vacuo and then, dichloromethane and ammonium chloride (10% aqueous solution) were added. The mixture was filtered through a diatomaceous earth cartridge. The solvent was then evaporated in vacuo and the residue was purified by CC-TLC (centrifugal circular thin-layer chromatography) on a chromatotron (a preparative, centrifugally accelerated, radial, thin-layer chromatograph). The crude product was crystallised from diethyl ether/heptane to yield E3 (0.037 g, 52%) as a solid. C$_{22}$H$_{19}$F$_5$N$_4$ requires 434; Found 435 (MH$^+$).

Melting point: 138.8° C.

$^1$H NMR (400 MHz, chloroform –d) δ ppm: 2.56-2.62 (m, 4H), 3.54 (s, 2H), 3.78-3.85 (m, 4H), 6.72 (tt, J=8.91, 2.28 Hz, 1H), 6.71 (s, 1H), 6.86-6.95 (m, 2H), 7.28-7.35 (m, 2H), 7.41-7.51 (m, 3H).

Example 4 cis-6-(3,5-Dimethylpiperazin-1-yl)-4-phenyl-3-trifluoromethyl-pyridazine (E4)

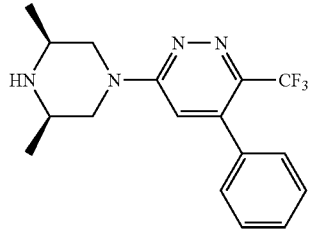 [SMILES: C[C@@H]1CN(c2cc(-c3ccccc3)c(C(F)(F)F)nn2)C[C@H](C)N1]

A mixture of 6-chloro-4-phenyl-3-trifluoromethyl-pyridazine (D3) (0.15 g, 0.58 mmol), 2,6-cis-dimethylpiperazine (0.097 g, 0.87 mmol) and diisopropylethylamine (0.202 ml, 1.16 mmol) in acetonitrile (3 ml) was stirred at 180° C. for 30 min., under microwave irradiation. The solvent was evaporated in vacuo and then dichloromethane and a saturated solution of ammonium chloride were added. The mixture was filtered and the solvent evaporated in vacuo. The residue was purified by column chromatography (silica gel; 1-3% ammonia in methanol (7M)/dichloromethane). The desired fractions were collected and evaporated in vacuo. The product thus obtained was treated with a solution of hydrochloric acid in diethyl ether (2M) to yield the corresponding salt E4 (0.058 g, 27%; CIS) as a pale brown solid. C$_{17}$H$_{19}$F$_3$N$_4$.HCl; free base requires 336; Found 337 (MH$^+$).

Melting point (ether): 285.4° C.

$^1$H NMR (400 MHz, DMSO-d$_6$) δ ppm: 1.32 (d, J=6.63 Hz, 6H), 3.08 (dd, J=13.99, 11.51 Hz, 2H), 3.30-3.41 (m, 2H), 4.76 (d, J=13.27 Hz, 2H), 7.36-7.43 (m, 3H), 7.49-7.55 (m, 3H), 9.16-9.27 (m, 1H), 9.60 (d, J=9.74 Hz, 1H).

Example 5

2-(5-Phenyl-6-trifluoromethyl-pyridazin-3-yl)-octahydro-pyrrolo[1,2-a]pyrazine (E5)

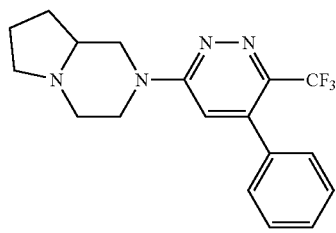 [SMILES: FC(F)(F)c1nnc(N2CCN3CCCC3C2)cc1-c1ccccc1]

A mixture of 6-chloro-4-phenyl-3-trifluoromethyl-pyridazine (D3) (0.10 g, 0.39 mmol), octahydro-pyrrolo[1,2-a]pyrazine, racemic mixture, (0.053 g, 0.42 mmol) and diisopropylethylamine (0.103 ml, 0.585 mmol) in acetonitrile (3 ml) was stirred at 150° C. for 30 min., under microwave irradiation. The reaction mixture was then diluted with dichloromethane (25 ml) and extracted with a saturated solution of sodium carbonate (12 ml). The organic layers were separated, dried (Na$_2$SO$_4$), filtered and the solvent evaporated in vacuo. The residue was then purified by column chromatography (silica gel; 0-2.5% ammonia in methanol (7M)/dichloromethane). The desired fractions were collected and evaporated in vacuo. The residue was precipitated from acetonitrile/heptane. The product obtained was treated with a solution of hydrochloric acid in diethyl ether (2M) to yield the corresponding salt E5 (0.081 g, 54%) as a white solid. C$_{18}$H$_{19}$F$_3$N$_4$.HCl; free base requires 348; Found 349 (MH$^+$).

Melting point: 104.2° C.

$^1$H NMR (500 MHz, DMSO-d$_6$) δ ppm: 1.71-2.25 (m, 3.5H), 2.88-3.01 (m, 0.5H), 3.06-3.19 (m, 0.5H), 3.19-3.60 (m, 4.5H), 3.65 (d, J=11.85 Hz, 0.5H), 3.83-3.98 (m, 2H), 4.26-4.37 (m, 0.5H), 4.86 (d, J=14.16 Hz, 0.5H), 5.00 (d, J=13.29 Hz, 0.5H), 7.28 (s, 0.5H), 7.37-7.46 (m, 2.5H), 7.47-7.57 (m, 3H), 11.74 (s, 0.5H), 11.87 (s, 0.5H).

Example 6

4-(4-Fluorophenyl)-6-piperazin-1-yl-3-trifluoromethyl-pyridazine (E6)

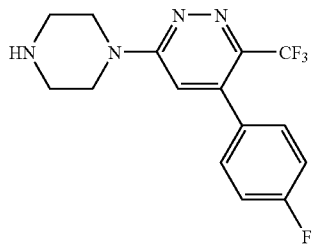 [SMILES: Fc1ccc(-c2cc(N3CCNCC3)nnc2C(F)(F)F)cc1]

To a solution of 4-[5-(4-fluorophenyl)-6-trifluoromethyl-pyridazin-3-yl]-piperazine-1-carboxylic acid tert-butyl ester (D8) (1.25 g, 2.93 mmol) in methanol (50 ml) was added Amberlyst® 15 ion exchange resin, acidic form (4.1 mmol/g) (3.6 g, 14.64 mmol) and the reaction mixture was shaken at room temperature for 18 h. After this period, the mixture was filtered and then a saturated solution of ammonia in methanol was added. The mixture was shaken for 1 h, filtered and the filtrate evaporated in vacuo. The crude product was purified by HPLC. The desired fractions were collected and evaporated in vacuo to yield E6 (0.507 g, 53%). C$_{15}$H$_{14}$F$_4$N$_4$ requires 326; Found 327 (MH$^+$).

Melting point: 137.4° C.

$^1$H NMR (400 MHz, Chloroform-d) δ ppm: 1.67 (br. s., 1H), 2.99-3.05 (m, 4H), 3.74-3.82 (m, 4H), 6.68 (s, 1H), 7.15 (t, J=8.71 Hz, 2H), 7.31 (dd, J=8.50, 5.39 Hz, 2H).

Example 7

6-piperazin-1-yl-4-thiophen-3-yl-3-trifluoromethyl-pyridazine (E7)

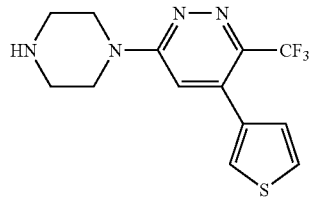 [SMILES: FC(F)(F)c1nnc(N2CCNCC2)cc1-c1ccsc1]

To a solution of 4-[5-(3-thienyl)-6-trifluoromethyl-pyridazin-3-yl]-piperazine-1-carboxylic acid tert-butyl ester (0.074 g, 0.18 mmol), prepared by procedures similar to those described for D8, in methanol (5 ml) was added Amberlyst® 15 ion exchange resin, acidic form (4.1 mmol/g) (0.218 g, 0.89 mmol) and the reaction mixture was shaken at room temperature for 18 h. After this period, the mixture was filtered and then a saturated solution of ammonia in methanol was added. The mixture was shaken for 1 h, filtered and the filtrate evaporated in vacuo. The crude product was crystallized from ether/heptane to yield E7 (0.049 g, 87%). C$_{13}$H$_{13}$F$_3$N$_4$S requires 314; Found 315 (MH$^+$).

Melting point (ether/heptane): 244.3° C.

$^1$H NMR (400 MHz, chloroform-d) δ ppm: 1.68 (br. s., 1H), 2.98-3.05 (m, 4H), 3.73-3.81 (m, 4H), 6.78 (s, 1H), 7.14-7.21 (m, 1H), 7.36-7.45 (m, 2H).

Example 8

6-piperazin-1-yl-4-o-tolyl-3-trifluoromethyl-pyridazine (E8)

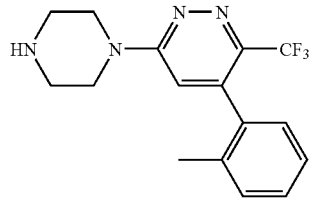 [SMILES: Cc1ccccc1-c1cc(N2CCNCC2)nnc1C(F)(F)F]

To a solution of 4-[5-(2-tolyl)-6-trifluoromethyl-pyridazin-3-yl]-piperazine-1-carboxylic acid tert-butyl ester (D11) (0.089 g, 0.21 mmol) in methanol (7 ml) was added Amberlyst® 15 ion exchange resin, acidic form (4.1 mmol/g) (0.257 g, 1.05 mmol) and the reaction mixture was shaken at room temperature for 18 h. After this period, the mixture was filtered and then a saturated solution of ammonia in methanol was added. The mixture was shaken for 1 h, filtered and the filtrate evaporated in vacuo. The residue was purified by HPLC and the desired fractions were collected and evaporated in vacuo to yield E8 (0.026 g, 50%) as a white solid. C$_{16}$H$_{17}$F$_3$N$_4$ requires 322; Found 323 (MH$^+$).

$^1$H NMR (400 MHz, DMSO-d$_6$) δ ppm: 2.05 (s, 3H), 2.74-2.83 (m, 4H), 3.37 (br. s., 1H), 3.62-3.72 (m, 4H), 7.15 (t, J=3.63 Hz, 2H), 7.26 (td, J=7.26, 1.66 Hz, 1H), 7.31-7.38 (m, 2H).

Example 9

4-(4'-Fluorobiphenyl-4-yl)-6-piperazin-1-yl-3-trifluoromethyl-pyridazine (E9)

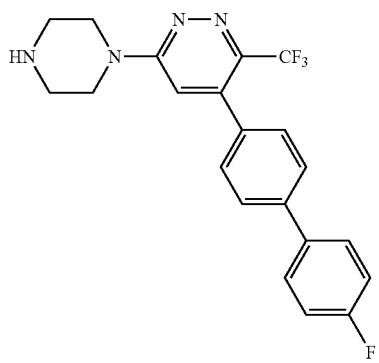 [SMILES: Fc1ccc(-c2ccc(-c3cc(N4CCNCC4)nnc3C(F)(F)F)cc2)cc1]

A mixture of 4-[5-(4'-fluorobiphenyl-4-yl)-6-trifluoromethyl-pyridazin-3-yl]-piperazine-1-carboxylic acid tert-butyl ester (D12) (0.115 g, 0.23 mmol) and trifluoroacetic acid (2 ml) in dichloromethane (8 ml) was stirred at room temperature for 2 h. The solvent was evaporated in vacuo and then, dichloromethane and a saturated solution of sodium carbonate were added. The organic layers were separated, dried ($Na_2SO_4$), filtered and the solvent evaporated in vacuo. The residue was then purified by column chromatography (silica gel; 1-3% ammonia in methanol (7M)/dichloromethane). The desired fractions were collected and evaporated in vacuo to yield E9 (0.084 g, 91%). $C_{21}H_{18}F_4N_4$ requires 402; Found 403 ($MH^+$).

Melting point: 161.9° C.
$^1$H NMR (400 MHz, chloroform-d) δ ppm: 1.72 (br. s., 1H), 2.99-3.05 (m, 4H), 3.75-3.82 (m, 4H), 6.74 (s, 1H), 7.13-7.20 (m, 2H), 7.40 (d, J=8.29 Hz, 2H), 7.57-7.64 (m, 4H).

Example 10

4-Phenyl-6-piperazin-1-yl-pyridazine-3-carbonitrile (E 10)

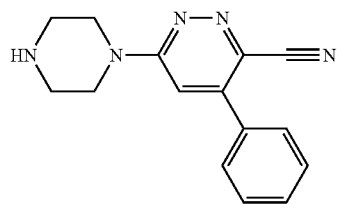 [SMILES: N#Cc1nnc(N2CCNCC2)cc1-c1ccccc1]

To a solution of 4-(6-cyano-5-phenyl-pyridazin-3-yl)-piperazine-1-carboxylic acid tert-butyl ester (D14) (0.133 g, 0.37 mmol) in methanol (10 ml) was added Amberlyst® 15 ion exchange resin, acidic form (4.1 mmol/g) (1.3 g, 5.3 mmol) and the reaction mixture was shaken at room temperature for 18 h. After this period, the mixture was filtered and then a saturated solution of ammonia in methanol was added. The mixture was shaken for 1 h, filtered and the filtrate evaporated in vacuo. The residue was purified by HPLC. The desired fractions were collected and evaporated in vacuo to yield E10 (0.06989 g, 72%) as a white solid. $C_{15}H_{15}N_5$ requires 265; Found 266 ($MH^+$).

Melting point: 271.6° C.
$^1$H NMR (400 MHz, DMSO-$d_6$) δ ppm: 2.77-2.84 (m, 4H), 3.34 (br. s., 1H), 3.71-3.80 (m, 4H), 7.29 (s, 1H), 7.55-7.61 (m, 3H), 7.66-7.72 (m, 2H).

Example 27

4-(5-Chloro-thiophen-2-yl)-6-piperazin-1-yl-3-trifluoromethyl-pyridazine (E27)

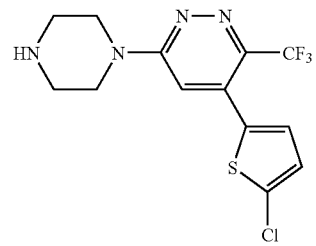 [SMILES: FC(F)(F)c1nnc(N2CCNCC2)cc1-c1ccc(Cl)s1]

To a solution of 4-[5-(5-chloro-thiophen-2-yl)-6-trifluoromethyl-pyridazin-3-yl]-piperazine-1-carboxylic acid tert-butyl ester (D15) (0.114 g, 0.25 mmol) in methanol (10 ml) was added Amberlyst® 15 ion exchange resin, acidic form (4.1 mmol/g) (0.305 g, 1.25 mmol) and the reaction mixture was shaken at room temperature for 18 h. After this period, the mixture was filtered and then a saturated solution of ammonia in methanol was added. The mixture was shaken for 1 h, filtered and the filtrate evaporated in vacuo. The residue was then purified by column chromatography (silica gel; 3% ammonia in methanol (7M)/dichloromethane). The desired fractions were collected and evaporated in vacuo. The crude product was dissolved in a 2 M solution of hydrochoric acid in diethyl ether and the mixture stirred at room temperature for 16. The solvent was evaporated in vacuo. The solid obtained was triturated from diethyl ether to yield E27 (0.062 g, 87%). $C_{13}H_{12}ClF_3N_4S$ requires 348; Found 349 ($MH^+$).

Melting point: Decomposes
$^1$H NMR (500 MHz, DMSO-$d_6$) δ ppm 3.24 (br. s., 4H) 4.07 (d, J=5.2 Hz, 4H) 7.23 (d, J=3.8 Hz, 1H) 7.26 (d, J=3.8 Hz, 1H) 7.41 (s, 1H) 9.45 (br. s., 2H).

Example 40

4-Phenyl-6-piperazin-1-yl-3-trifluoromethyl-pyridazine monohydrochloride (E40)

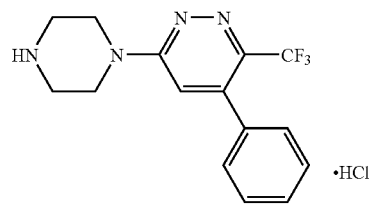 [SMILES: FC(F)(F)c1nnc(N2CCNCC2)cc1-c1ccccc1 ; Cl]

To a solution of E1 (16 g, 51.90 mmol) in 2-butanone (400 ml) warmed to 50° C. was added dropwise, hydrochloric acid in 2-propanol (6N, 51.90 mmol). The mixture was heated at reflux temperature for 90 minutes and then stirred for 2 hours at 50° C. and further overnight at room temperature. The precipitated crystals were filtered off and dried under vacuum at 45° C., to yield E40 (10.4 g, 58%).

Melting point: >185° C. (decomposes).

The following Examples (E11-E 19) were prepared by procedures similar to those described for Example (E6). Example (E20) was prepared by deprotection of Description (D13) according to a procedure analogous to the one reported for Example (E1). Example (E28) was prepared in analogy to (E27) but using potassium carbonate as base and 1,4-dioxane as solvent. Examples (E29) (toluene/ethanol/H₂O), (E30) (toluene/ethanol/H₂O), (E31) (1,4-dioxane/H₂O), (E32) (1,4-dioxane/H₂O), (E33) (1,4-dioxane/H₂O), (E34) (1,4-dioxane/H₂O) and (E35) (1,4-dioxane/H₂O) were prepared by procedures similar to those described for Example (E27) but using the solvents specified for each case respectively. Examples (E18, E27, E28, E31, E32, E33 and E34) were isolated as hydrochloric acid salts.

The value in the column M.Wt free base, is the exact mass calculated using the exact masses of the most abundant isotopes.

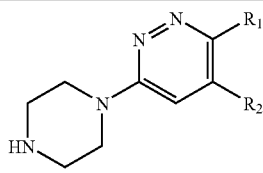

| Ex. | R¹ | R² | Melting Point (° C.) | Molecular Formula | M.Wt Free base | MH+ | RT (min) | LCMS Method |
|---|---|---|---|---|---|---|---|---|
| E1 | $CF_3$ | phenyl | 130.7 | $C_{15}H_{15}F_3N_4$ | 308 | 309 | 3.13 | 1 |
| E6 | $CF_3$ | 4-fluorophenyl | 137.4 | $C_{15}H_{14}F_4N_4$ | 326 | 327 | 3.39 | 1 |
| E7 | $CF_3$ | thiophen-3-yl | 244.3 | $C_{13}H_{13}F_3N_4S$ | 314 | 315 | 2.92 | 1 |
| E8 | $CF_3$ | 2-methylphenyl | nd | $C_{16}H_{17}F_3N_4$ | 322 | 323 | 3.37 | 2 |
| E9 | $CF_3$ | 4'-fluorobiphenyl | 161.9 | $C_{21}H_{18}F_4N_4$ | 402 | 403 | 4.65 | 1 |
| E10 | CN | phenyl | 271.6 | $C_{15}H_{15}N_5$ | 265 | 266 | 2.07 | 1 |
| E11 | $CF_3$ | 4-methylphenyl | 110.6 | $C_{16}H_{17}F_3N_4$ | 322 | 323 | 3.67 | 1 |

-continued
| Ex. | R¹ | R² | Melting Point (° C.) | Molecular Formula | M.Wt Free base | MH+ | RT (min) | LCMS Method |
|---|---|---|---|---|---|---|---|---|
| E12 | CF$_3$ |  | 198.2 | C$_{15}$H$_{14}$ClF$_3$N$_4$ | 342 | 343 | 3.74 | 1 |
| E13 | CF$_3$ | 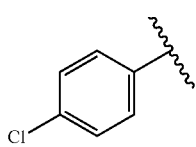 [SMILES: *c1ccc(Cl)cc1] | nd | C$_{15}$H$_{15}$F$_3$N$_4$O | 324 | 325 | 2.26 | 1 |
| E14 | CF$_3$ | 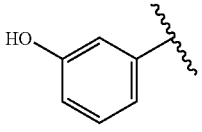 [SMILES: *c1cccc(O)c1] | 138.2 | C$_{15}$H$_{14}$BrF$_3$N$_4$ | 386 | 387 | 3.99 | 1 |
| E15 | CF$_3$ | 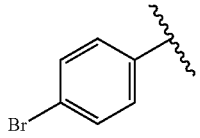 [SMILES: *c1ccc(Br)cc1] | 144.7 | C$_{15}$H$_{14}$F$_4$N$_4$ | 326 | 327 | 3.32 | 3 |
| E16 | CF$_3$ | 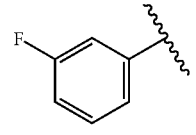 [SMILES: *c1cccc(F)c1] | 178.8 | C$_{15}$H$_{14}$ClF$_3$N$_4$ | 342 | 343 | 3.66 | 1 |
| E17 | CF$_3$ | 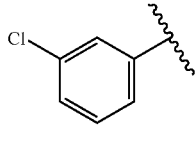 [SMILES: *c1cccc(Cl)c1] | 128.1 | C$_{19}$H$_{17}$F$_3$N$_4$ | 358 | 359 | 4.01 | 1 |
| E18 | CF$_3$ | 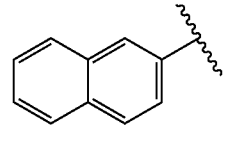 [SMILES: *c1ccc2ccccc2c1] | 281.8 | C$_{19}$H$_{17}$F$_3$N$_4$·HCl | 358 | 359 | 3.75 | 1 |
| E19 | CF$_3$ | 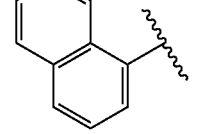 | 112.6 | C$_{13}$H$_{13}$F$_3$N$_4$S | 314 | 315 | 2.83 | 1 |

-continued
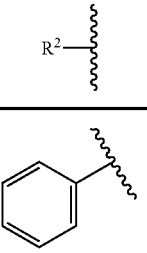
| Ex. | R¹ | R² | Melting Point (° C.) | Molecular Formula | M.Wt Free base | MH+ | RT (min) | LCMS Method |
|---|---|---|---|---|---|---|---|---|
| E20 | Cl | 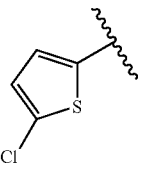 [SMILES: *c1ccc(Cl)s1] | 173.9 | $C_{14}H_{15}ClN_4$ | 274 | 275 | 2.29 | 4 |
| E27 | $CF_3$ | 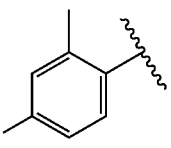 | decomposes | $C_{13}H_{12}ClF_3N_4S \cdot HCl$ | 348 | 349 | 3.55 | 4 |
| E28 | $CF_3$ | 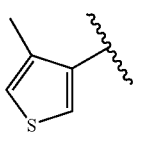 [SMILES: *c1cscc1C] | decomposes | $C_{16}H_{16}F_4N_4 \cdot HCl$ | 340 | 341 | 3.39 | 4 |
| E29 | $CF_3$ | 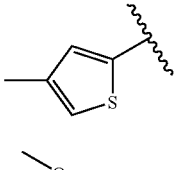 | 101.0 | $C_{14}H_{15}F_3N_4S$ | 328 | 329 | 3.07 | 4 |
| E30 | $CF_3$ | 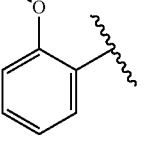 | 98.1 | $C_{14}H_{15}F_3N_4S$ | 328 | 329 | 3.30 | 4 |
| E31 | $CF_3$ | 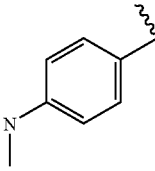 | 287.7 | $C_{16}H_{17}F_3N_4O \cdot HCl$ | 338 | 339 | 4.39 | 6 |
| E32 | $CF_3$ | 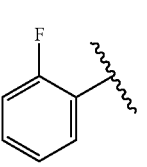 [SMILES: *c1ccccc1F] | 198.7 | $C_{17}H_{20}F_3N_5 \cdot HCl$ | 351 | 352 | 4.13 | 6 |
| E33 | $CF_3$ |  | decomposes | $C_{15}H_{14}F_4N_4 \cdot HCl$ | 326 | 327 | 4.41 | 6 |

-continued

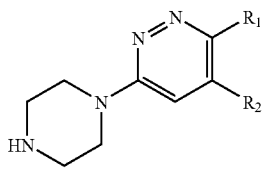

| Ex. | R¹ | R² | Melting Point (° C.) | Molecular Formula | M.Wt Free base | MH+ | RT (min) | LCMS Method |
|---|---|---|---|---|---|---|---|---|
| E34 | $CF_3$ | 2,5-dichlorophenyl | 286.3 | $C_{15}H_{13}Cl_2F_3N_4 \cdot HCl$ | 376 | 377 | 4.83 | 6 |
| E35 | $CF_3$ | biphenyl-4-yl | 199.1 | $C_{21}H_{19}F_3N_4$ | 384 | 385 | 4.00 | 7 |

Example (E21) was prepared by a procedure similar to the one described for (E3), examples (E22, E24 and E25) were prepared by procedures similar to those described for (E2), (E23) was prepared from (E1) by reductive amination with (1-ethoxycyclopropoxy)trimethylsilane following the procedure described in Gillaspy, M. L.; Lefker, B. A; Hada, W. A.; Hoover, D. J. Tetrahedron Letters 1995, 36, 7399-7402, E(26) was prepared by a procedure similar to the one those described for (E4) and examples (E36, E37, E38 and E39) were prepared by procedures similar to (E2) but using the hydrochloric acid salt of E1 as starting material, dichloromethane as solvent and triethyl amine, respectively. Examples (E2), (E4), (E5), (E22) and (E26) were isolated as hydrochloric acid salts. Examples (E5) and (E26) (trans) were obtained as racemic mixtures.

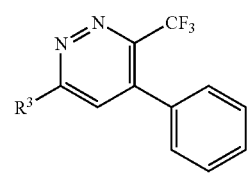

| Ex. | R³ | Melting Point (° C.) | Molecular Formula | M.Wt Free base | MH+ | RT (min) | LCMS Method |
|---|---|---|---|---|---|---|---|
| E2 | 4-ethylpiperazin-1-yl | 281.9 | $C_{17}H_{19}F_3N_4 \cdot HCl$ | 336 | 337 | 4.23 | 1 |
| E3 | 4-(3,5-difluorobenzyl)piperazin-1-yl | 138.8 | $C_{22}H_{19}F_5N_4$ | 434 | 435 | 5.57 | 1 |

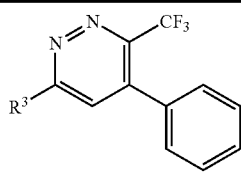

| Ex. | R³ | Melting Point (° C.) | Molecular Formula | M.Wt Free base | MH+ | RT (min) | LCMS Method |
|---|---|---|---|---|---|---|---|
| E4 | (2,6-dimethylpiperazinyl) | 285.4 | C₁₇H₁₉F₃N₄•HCl | 336 | 337 | 4.05 | 5 |
| E5 | (octahydropyrrolo[1,2-a]pyrazinyl) | 104.2 | C₁₈H₁₉F₃N₄•HCl | 348 | 349 | 4.38 | 1 |
| E21 | 4-(3,4-difluorobenzyl)piperazinyl | 185.1 | C₂₂H₁₉F₅N₄ | 434 | 435 | 5.49 | 1 |
| E22 | 4-methylpiperazinyl | 163.3 | C₁₆H₁₇F₃N₄•HCl | 322 | 323 | 3.95 | 1 |
| E23 | 4-cyclopropylpiperazinyl | 152.0 | C₁₈H₁₉F₃N₄ | 348 | 349 | 4.75 | 1 |
| E24 | 4-propylpiperazinyl | 129.8 | C₁₈H₂₁F₃N₄ | 350 | 351 | 4.64 | 4 |
| E25 | 4-butylpiperazinyl | 102.9 | C₁₉H₂₃F₃N₄ | 364 | 365 | 5.05 | 4 |
| E26 | 2,5-dimethylpiperazinyl (MIXTURE OF TRANS) | 273.0 | C₁₇H₁₉F₃N₄•HCl | 336 | 337 | 3.99 | 5 |

-continued

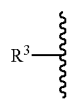

| Ex. | R³—⌇ | Melting Point (°C.) | Molecular Formula | M.Wt Free base | MH+ | RT (min) | LCMS Method |
|---|---|---|---|---|---|---|---|
| E36 | 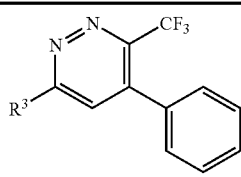 | nd | $C_{22}H_{21}F_3N_4$ | 398 | 399 | 3.83 | 7 |
| E37 | 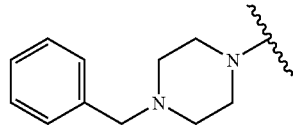 [SMILES: *N1CCN(Cc2ccccc2)CC1] | nd | $C_{21}H_{20}F_3N_5$ | 399 | 400 | 4.49 | 6 |
| E38 | 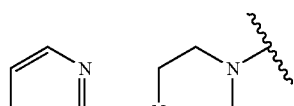 | nd | $C_{21}H_{20}F_3N_5$ | 399 | 400 | 4.77 | 6 |
| E39 | 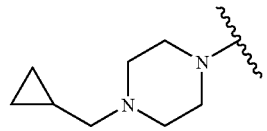 [SMILES: *N1CCN(CC2CC2)CC1] | nd | $C_{19}H_{21}F_3N_4$ | 362 | 363 | 4.69 | 6 |

Pharmacology

In Vitro Binding Affinity for Human $D2_L$ Receptor

Frozen membranes of human Dopamine D2L receptor-transfected CHO cells were thawed, briefly homogenised using an Ultra-Turrax T25 homogeniser and diluted in Tris-HCl assay buffer containing NaCl, CaCl$_2$, MgCl$_2$, KCl (50, 120, 2, 1, and 5 mM respectively, adjusted to pH 7.7 with HCl) to an appropriate protein concentration optimised for specific and non-specific binding. Radioligand [$^3$H]Spiperone (NEN, specific activity ~70 Ci/mmol) was diluted in assay buffer at a concentration of 2 nmol/L. Prepared radioligand (50 μl), along with 50 μl of either the 10% DMSO control, Butaclamol ($10^{-6}$ mol/l final concentration), or compound of interest, was then incubated (30 min, 37° C.) with 400 μl of the prepared membrane solution. Membrane-bound activity was filtered through a Packard Filtermate harvester onto GF/B Unifilterplates and washed with ice-cold Tris-HCl buffer (50 mM; pH 7.7; 6×0.5 ml). Filters were allowed to dry before adding scintillation fluid and counting in a Topcount scintillation counter. Percentage specific bound and competition binding curves were calculated using S-Plus software (Insightful). Most compounds had a pIC$_{50}$ value>5.0.

Fast Dissociation

Compounds showing an IC$_{50}$ less than 10 μM were tested in an indirect assay adapted from a method published by Josee E. Leysen and Walter Gommeren, Journal of Receptor Research, 1984, 4(7), 817-845, to evaluate their rate of dissociation. Compounds at a concentration of 4 times their IC$_{50}$ were first incubated for one hour with human D2L receptor cell membranes in a volume of 2 ml at 25° C., then filtered over glass-fibre filter under suction using a 40 well multividor. Immediately after, the vacuum was released. 0.4 ml of pre-warmed buffer (25° C.) containing 1 nM [$^3$H]spiperone was added on the filter for 5 minutes. The incubation was stopped by initiating the vacuum and immediate rinsing with 2×5 ml of ice-cold buffer. The filter-bound radioactivity was measured in a liquid scintillation spectrometer. The principle of the assay is based on the assumption that the faster a compound dissociates from the D2 receptor, the faster [$^3$H] spiperone binds to the D2 receptor. For example, when D2 receptors are incubated with clozapine at the concentration of 1850 nM (4×IC$_{50}$), [$^3$H]spiperone binding is equivalent to 60-70% of its total binding capacity (measured in absence of drug) after 5 min incubation on filter. When incubated with other antipsychotics, [$^3$H]spiperone binding varies between 20 and 50%. Since clozapine was included in each filtration run, tested compounds were considered fast dissociating D2 antagonists if they were dissociating as fast or faster than clozapine. Most tested compounds had a dissociation rate faster than that of clozapine, i.e. >50%.

In Vitro Binding Affinity for Human D3 Receptor

Frozen membranes of human Dopamine D3 receptor-transfected CHO cells were thawed, briefly homogenized using an Ultra-Turrax T25 homogeniser and diluted in 50 mM Tris-HCl assay buffer containing 120 mM NaCl, 2 mM CaCl$_2$, 1 mM MgCl$_2$, 5 mM KCl and 0.1% BSA (adjusted to pH 7.4 with HCl) to an appropriate protein concentration optimized for specific and non-specific binding. Radioligand [$^{125}$I]Iodosulpride (Amersham, specific activity ~2000 Ci/mmol) was diluted in assay buffer at a concentration of 2 nM. Prepared radioligand (20 μl), along with 40 μl of either the 10% DMSO control, Risperidone (10$^{-6}$M final concentration), or compound of interest, was then incubated with 70 μl of the prepared membrane solution and 70 μl of WGA coated PVT beads (0.25 mg/well final concentration). After shaking for 24 hours at RT plates were counted in a Topcount™ scintillation counter. Percentage specific binding and competition binding curves were calculated using S-Plus software (Insightful).

In Vitro Binding Affinity for Human 5HT6 Receptor

Frozen membranes of human Serotonin 5HT6 receptor-transfected HEK cells were thawed, briefly homogenized using an Ultra-Turrax T25 homogeniser and diluted in 50 mM Tris-HCl assay buffer containing 10 mM MgCl$_2$, 1 mM EDTA and 10 μM Pargyline (adjusted to pH 7.4 with HCl) to an appropriate protein concentration optimized for specific and non-specific binding. Radioligand [$^{3}$H]Lysergic acid diethylamide (Perkin Elmer, specific activity ~80 Ci/mmol) was diluted in assay buffer at a concentration of 20 nM. Radioligand (20 μl), along with 40 μl of either the 10% DMSO control, Methiothepine (10$^{-5}$ M final concentration), or compound of interest, was then incubated with 70 μl of the prepared membrane solution and 70 μl of WGA coated PVT beads (0.25 mg/well final concentration). After shaking for 24 hours at RT plates were counted in a Topcount™ scintillation counter. Percentage specific binding and competition binding curves were calculated using S-Plus software (Insightful).

| Ex. | D2$_L$ binding pIC$_{50}$ | D2 dissociation | 5-HT6 binding pIC$_{50}$ | D3 binding pIC$_{50}$ |
|---|---|---|---|---|
| E20 | 5.85 | n.d. | 5.36 | 6.82 |
| E21 | 5.70 | n.d. | >5 | 5.83 |
| E1 | 5.96 | 75% | 6.23 | 7.18 |
| E3 | 6.21 | n.d. | >5 | <5 |
| E6 | 6.43 | 55% | 6.67 | 7.44 |
| E13 | 5.29 | n.d. | 5.45 | <5 |
| E4 | 5.42 | n.d. | 5.07 | <5 |
| E26 | 5.22 | n.d. | 5.64 | <5 |
| E14 | 5.39 | n.d. | 5.37 | <5 |
| E11 | 5.90 | n.d. | 6.13 | 7.05 |
| E7 | 6.06 | 81% | 5.81 | <5 |
| E10 | 5.25 | 86% | 5.34 | <5 |
| E15 | 5.24 | n.d. | 5.81 | 6.2 |
| E22 | 6.11 | 79% | 5.90 | 7.41 |
| E2 | 6.69 | 80.5% | 5.50 | 7.60 |
| E12 | 5.44 | n.d. | 5.76 | 6.46 |
| E23 | 5.73 | n.d. | <5 | 6.56 |
| E16 | 5.32 | n.d. | 6.61 | 6.26 |
| E17 | 5.10 | n.d. | 6.36 | 6.40 |
| E19 | 5.86 | n.d. | 5.71 | 6.83 |
| E18 | 5.11 | n.d. | 6.80 | <5 |
| E8 | 6.00 | 78.5% | 6.58 | <5 |
| E9 | 6.10 | 48% | 5.74 | 7.32 |
| E5 | 5.90 | 84% | 5.99 | <5 |
| E25 | 7.16 | 47% | 5.57 | 8.58 |
| E24 | 7.17 | n.d. | 5.27 | <5 |
| E27 | 5.82 | n.d. | 6.10 | <5 |
| E28 | 6.43 | n.d. | 6.61 | 7.32 |
| E29 | 5.45 | n.d. | 6.27 | <5 |
| E30 | 6.12 | 82% | 6.25 | 7.27 |
| E36 | 7.48 | n.d. | 5.18 | <5 |
| E37 | 6.25 | n.d. | <5 | 6.75 |
| E38 | 6.55 | n.d. | <5 | 7.06 |
| E39 | 7.22 | n.d. | 5.41 | <5 |
| E31 | <5 | n.d. | 5.95 | 6.32 |
| E32 | <5 | n.d. | 6.01 | 5.89 |
| E33 | 5.91 | n.d. | 5.89 | 7.28 |
| E34 | 5.33 | n.d. | 6.10 | 7.06 |
| E35 | 5.57 | n.d. | 5.82 | 6.97 | n.d.: not determined

The invention claimed is:

1. A compound of formula (I)

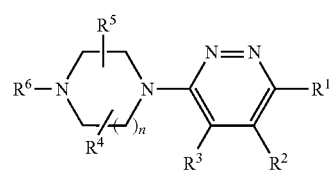

or a stereoisomeric form thereof, wherein
R$^1$ is trifluoromethyl;
R$^2$ is selected from the group consisting of phenyl; phenyl substituted with 1, 2 or 3 substituents each independently selected from the group consisting of halo, cyano, C$_{1-4}$alkyl, C$_{1-4}$alkyloxy, C$_{1-4}$alkylsulfonyl, perfluoro C$_{1-4}$alkyl, diC$_{1-4}$alkylamino, hydroxyl, and phenyl substituted with 1, 2 or 3 substituents each independently selected from the group consisting of halo, C$_{1-4}$alkyl and perfluoroC$_{1-4}$alkyl; thienyl; thienyl substituted with 1 or 2 substituents each independently selected from the group consisting of halo and C$_{1-4}$alkyl; naphthyl; pyridinyl; pyrrolyl; benzothiazolyl; indolyl; quinolinyl; C$_{3-8}$cycloalkyl; or C$_{5-7}$cycloalkenyl;
R$^3$ is hydrogen;
R$^4$ and R$^5$ are each independently selected from the group consisting of hydrogen or methyl;
n is 1;
R$^6$ is selected from the group consisting of hydrogen, ethyl or (3,5-difluorophenyl)methyl;
or R$^5$ and R$^6$ together form 1,3-propanediyl;
or a pharmaceutically acceptable salt thereof.

2. A compound according to claim 1 wherein the compound is 4-phenyl-6-piperazin-1-yl-3-trifluoromethyl-pyridazine.

3. A compound according to claim 1 wherein the compound is 4-phenyl-6-piperazin-1-yl-3-trifluoromethyl-pyridazine monohydrochloride.

4. A pharmaceutical composition comprising a therapeutically effective amount of a compound as defined in claim 1.

* * * * *